(12) United States Patent
Heymann et al.

(10) Patent No.: US 10,703,813 B2
(45) Date of Patent: Jul. 7, 2020

(54) ANTI IL-34 ANTIBODIES

(71) Applicants: Universite de Nantes, Nantes (FR); Chu Nantes, Nantes (FR); Institut National de la Sante et de la Recherche Medicale (INSERM), Paris (FR)

(72) Inventors: Dominique Heymann, Indre (FR); Aude Segaliny, Dammarie (FR); Régis Brion, Chantonnay (FR)

(73) Assignees: UNIVERSITE DE NANTES, Nantes (FR); CHU NANTES, Nantes (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 0 days.

(21) Appl. No.: 15/536,962

(22) PCT Filed: Dec. 21, 2015

(86) PCT No.: PCT/EP2015/080866
§ 371 (c)(1),
(2) Date: Jun. 16, 2017

(87) PCT Pub. No.: WO2016/097420
PCT Pub. Date: Jun. 23, 2016

(65) Prior Publication Data
US 2017/0342148 A1    Nov. 30, 2017

(30) Foreign Application Priority Data

Dec. 19, 2014 (EP) .................................... 14199494

(51) Int. Cl.
*A61K 39/395* (2006.01)
*C07K 16/24* (2006.01)
*C12N 15/24* (2006.01)
*G01N 33/68* (2006.01)

(52) U.S. Cl.
CPC ........ *C07K 16/244* (2013.01); *A61K 39/3955* (2013.01); *G01N 33/6869* (2013.01); *C07K 2317/24* (2013.01); *C07K 2317/565* (2013.01); *C07K 2317/76* (2013.01); *C07K 2317/92* (2013.01); *G01N 2333/54* (2013.01)

(58) Field of Classification Search
None
See application file for complete search history.

(56) References Cited

U.S. PATENT DOCUMENTS

| | | | |
|---|---|---|---|
| 4,444,887 A | 4/1984 | Hoffmann | |
| 4,716,111 A | 12/1987 | Osband et al. | |
| 5,530,101 A | 6/1996 | Queen et al. | |
| 5,545,806 A | 8/1996 | Lonberg et al. | |
| 5,565,332 A | 10/1996 | Hoogenboom et al. | |
| 5,585,089 A | 12/1996 | Queen et al. | |
| 5,639,641 A | 6/1997 | Pedersen et al. | |
| 5,641,870 A | 6/1997 | Rinderknecht et al. | |
| 5,772,997 A | 6/1998 | Hudziak et al. | |
| 5,792,632 A | 8/1998 | Dujon et al. | |
| 5,814,318 A | 9/1998 | Lonberg et al. | |
| 5,830,729 A | 11/1998 | Jaisser et al. | |
| 6,238,924 B1 | 5/2001 | Dujon et al. | |

FOREIGN PATENT DOCUMENTS

| | | | |
|---|---|---|---|
| EP | 0 239 400 | 9/1987 | |
| EP | 0 404 097 | 12/1990 | |
| EP | 0 519 596 | 12/1992 | |
| EP | 0 592 106 | 4/1994 | |
| WO | WO 91/01753 | 2/1991 | |
| WO | WO 91/09967 | 7/1991 | |
| WO | WO 91/10741 | 7/1991 | |
| WO | WO 93/11161 | 6/1993 | |
| WO | WO 96/33735 | 10/1996 | |
| WO | WO 96/34096 | 10/1996 | |
| WO | WO 98/16654 | 4/1998 | |
| WO | WO 98/24893 | 6/1998 | |
| WO | WO 98/46645 | 10/1998 | |
| WO | WO 98/50433 | 11/1998 | |
| WO | WO 03/025183 | 3/2003 | |
| WO | WO 2004/067753 | 8/2004 | |
| WO | WO 2009/054985 | 4/2009 | |
| WO | WO 2013/119176 | 8/2013 | |
| WO | WO-2013119716 A1 * | 8/2013 | ......... C07K 14/7153 |
| WO | WO 2014/001368 | 1/2014 | |

OTHER PUBLICATIONS

Mizuno et al., Am. J. Pathol., 2011, vol. 179(4):2016-2017.*
Knappik et al., J. Mol. Biol., 2000, vol. 296(1):57-86.*
International Search Report dated Apr. 19, 2016, in corresponding PCT Application No. PCT/EP2015/080866.
Cronk et al., *Microglia—the brain's busy bees*, 5(53) F1000PRIME Reports 1-10 (Dec. 3, 2013).
Dai et al., *Targeted disruption of the mouse-colony-stimulating factor 1 receptor gene results in osteopetrosis, mononuclear phagocyte deficiency, increased primitive progenitor cells frequencies, and reproductive defects*, 99(1) Blood 111-120 (Jan. 1, 2002).
Felix et al., *Human IL-34 and CSF-1 Establish Structurally Similar Extracellular Assemblies with Their Common Hematopoietic Receptor*, 21 Structure 528-539 (Apr. 2, 2013).
Foucher et al., *IL-34 Induces the Differentiation of Human Monocytes into Immunosuppressive Macrophages. Antagonistic Effects of GM-CSF and IFNγ*, 8(2) PLOS One 1-10 (Feb. 2013).
Lin et al., *Discovery of a Cytokine and Its Receptor by Functional Screening of the Extracellular Proteome*, 320 Science 807-811 (May 9, 2008).

(Continued)

*Primary Examiner* — Xiaozhen Xie
(74) *Attorney, Agent, or Firm* — Buchanan Ingersoll & Rooney PC

(57) ABSTRACT

The present disclosure relates to novel anti IL-34 antibodies or antigen-binding fragments thereof specifically binding cytokine IL-34 with high affinity, the method of obtaining of these antibodies and their therapeutic use.

17 Claims, 9 Drawing Sheets

Figure 1:
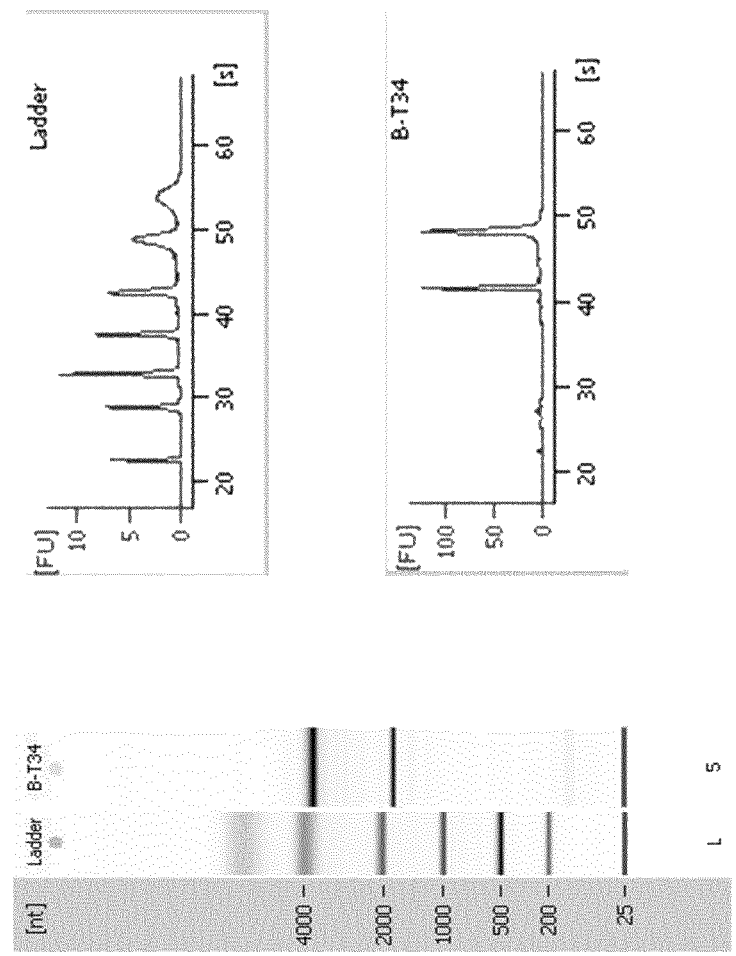

Specification includes a Sequence Listing.

(56) References Cited

OTHER PUBLICATIONS

Liu et al., *The mechanism of shared but distinct CSF-1R signaling by the non-homologous cytokines IL-34 and CSF-1*, 1824(7) Biochim Biophys Acta 938-945 (Jul. 2012).

Ma et al., *Structural Basis for the Dual Recognition of Helical Cytokines IL-34 and CSF-1 by CSF-1R*, 20 Structure 676-687 (Apr. 4, 2012).

Needleman et al., *A General Method Applicable to the Search for Similarities in the Amino Acid Sequence of Two Proteins*, 48 J. Mol. Biol. 443-453 (1970).

Pearson et al., *Improved tools for biological sequence comparison*, 85 Proc. Natl. Acad. Sci. 2444-2448 (Apr. 1988).

Ries et al., *Targeting Tumor-Associated Macrophages with Anti-CSF-1R Antibody Reveals a Strategy for Cancer Therapy*, 25 Cancer Cell 846-859 (Jun. 16, 2014).

Roth et al., *The Biology of CSF-1 and Its Receptor*, 181 Current Topics in Microbiology and Immunology 141-167 (1992) (pp. 141-142 provided) (if the Examiner seeks all pages, please ask Applicants' representative).

Ségaliny et al., *Interleukin-34 promotes tumor progression and metastatic process in osteosarcoma through induction of angiogenesis and macrophage recruitment*, 137 Int. J. Cancer 73-85 (2015).

Smith et al., *Comparative biosequence metrics*, 18(1) J. Mol Evol. 38-46 (1981) (abstract only).

Stanley et al., *CSF-1 Receptor Signaling in Myeloid Cells*, 2(6) Cold Spring Harbour Perspectives in Biology 1-21 (2014).

Tatusova et al., *BLAST 2 Sequences, a new tool for comparing protein and nucleotide sequences*, 174 FEMS Microbiology Letters 247-250 (1999).

Verhoeyen et al., *Engineering of Antibodies*, 8(2) BioEssays 74-78 (Feb./Mar. 1988).

Wang et al., *Interleukin-34, a cytokine crucial for the differentiation and maintenance of tissue resident macrophages and Langerhans cells*, 44(6) Eur. J. Immunol. 1575-1581 (Jun. 2014).

Wei et al., *Functional overlap but differential expression of CSF-1 and IL-34 in their CSF-1 receptor-mediated regulation of myeloid cells*, 88(3) J. Leukoc. Biol. 495-505 (2010).

Ye et al., *IgBLAST: an immunoglobulin variable domain sequence analysis tool*, 41 Nucleic Acids Research W34-W40 (2013).

\* cited by examiner

SEQUENCE LISTING

```
<160> NUMBER OF SEQ ID NOS: 16

<210> SEQ ID NO 1
<211> LENGTH: 16
<212> TYPE: PRT
<213> ORGANISM: Mus musculus
<220> FEATURE:
<221> NAME/KEY: misc_feature
<223> OTHER INFORMATION: CDR-L1 of murine anti-IL4 antibody

<400> SEQUENCE: 1

Arg Ser Ser Gln Thr Ile Val His Ser Asn Gly Lys Thr Tyr Leu Glu
1               5                   10                  15

<210> SEQ ID NO 2
<211> LENGTH: 7
<212> TYPE: PRT
<213> ORGANISM: Mus musculus
<220> FEATURE:
<221> NAME/KEY: misc_feature
<223> OTHER INFORMATION: CDR-L2 of murine anti-IL4 antibody

<400> SEQUENCE: 2

Lys Val Ser Asn Arg Phe Ser
1               5

<210> SEQ ID NO 3
```

```
<211> LENGTH: 9
<212> TYPE: PRT
<213> ORGANISM: Mus musculus
<220> FEATURE:
<221> NAME/KEY: misc_feature
<223> OTHER INFORMATION: CDR-L3 of murine anti-IL4 antibody

<400> SEQUENCE: 3

Phe Gln Gly Ser His Val Pro Leu Thr
1               5

<210> SEQ ID NO 4
<211> LENGTH: 5
<212> TYPE: PRT
<213> ORGANISM: Mus musculus
<220> FEATURE:
<221> NAME/KEY: misc_feature
<223> OTHER INFORMATION: CDR-H1 of murine anti-IL4 antibody

<400> SEQUENCE: 4

Asp Tyr Asn Met Asp
1               5

<210> SEQ ID NO 5
<211> LENGTH: 17
<212> TYPE: PRT
<213> ORGANISM: Mus musculus
<220> FEATURE:
<221> NAME/KEY: misc_feature
<223> OTHER INFORMATION: CDR-H2 of murine anti-IL4 antibody

<400> SEQUENCE: 5

Asp Ile Asn Pro Asn Tyr Glu Ser Thr Thr Tyr Asn Gln Lys Phe Lys
1               5                   10                  15

Gly

<210> SEQ ID NO 6
<211> LENGTH: 5
<212> TYPE: PRT
<213> ORGANISM: Mus musculus
<220> FEATURE:
<221> NAME/KEY: misc_feature
<223> OTHER INFORMATION: CDR-H3 of murine anti-IL4 antibody

<400> SEQUENCE: 6

Ser Gly Gly Asp Tyr
1               5

<210> SEQ ID NO 7
<211> LENGTH: 112
<212> TYPE: PRT
<213> ORGANISM: Mus musculus
<220> FEATURE:
<221> NAME/KEY: misc_feature
<223> OTHER INFORMATION: LIGHT CHAIN of murine anti-IL4 antibody

<400> SEQUENCE: 7

Asp Val Leu Met Thr Gln Thr Pro Leu Ser Leu Pro Val Gly Leu Gly
1               5                   10                  15

Asp Gln Ala Ser Ile Ser Cys Arg Ser Ser Gln Thr Ile Val His Ser
            20                  25                  30

Asn Gly Lys Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

<210> SEQ ID NO 8
<211> LENGTH: 114
<212> TYPE: PRT
<213> ORGANISM: Mus musculus
<220> FEATURE:
<221> NAME/KEY: misc_feature
<223> OTHER INFORMATION: HEAVY CHAIN of murine anti-IL4 antibody

<400> SEQUENCE: 8

Glu Val Gln Leu Gln Gln Phe Gly Ala Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Asp Ile Asn Pro Asn Tyr Glu Ser Thr Thr Tyr Asn Gln Lys Phe
    50                  55                  60

Lys Gly Lys Ala Thr Leu Thr Val Asp Arg Ser Ser Thr Ala Tyr
65                  70                  75                  80

Met Glu Leu Arg Ser Leu Thr Ser Glu Asp Thr Ala Val Tyr Tyr Cys
                85                  90                  95

Leu Arg Ser Gly Gly Asp Tyr Trp Gly Gln Gly Thr Thr Leu Thr Val
            100                 105                 110

Ser Ser

<210> SEQ ID NO 9
<211> LENGTH: 48
<212> TYPE: DNA
<213> ORGANISM: Mus musculus
<220> FEATURE:
<221> NAME/KEY: misc_feature
<223> OTHER INFORMATION: CDR-L1 of murine anti-IL4 antibody

<400> SEQUENCE: 9
agatctagtc agaccattgt acatagtaat ggaaagacct atttagaa          48

<210> SEQ ID NO 10
<211> LENGTH: 21
<212> TYPE: DNA
<213> ORGANISM: Mus musculus
<220> FEATURE:
<221> NAME/KEY: misc_feature
<223> OTHER INFORMATION: CDR-L2 of murine anti-IL4 antibody

<400> SEQUENCE: 10
aaagtttcca accgattttc t                                       21

<210> SEQ ID NO 11
<211> LENGTH: 27
<212> TYPE: DNA
<213> ORGANISM: Mus musculus
<220> FEATURE:
<221> NAME/KEY: misc_feature
<223> OTHER INFORMATION: CDR-L3 of murine anti-IL4 antibody

<400> SEQUENCE: 11

```
tttcaaggtt cacatgttcc gctcacg                                            27
```

<210> SEQ ID NO 12
<211> LENGTH: 48
<212> TYPE: DNA
<213> ORGANISM: Mus musculus
<220> FEATURE:
<221> NAME/KEY: misc_feature
<223> OTHER INFORMATION: CDR-H1 of murine anti-IL4 antibody

<400> SEQUENCE: 12

```
agatctagtc agaccattgt acatagtaat ggaaagacct atttagaa                     48
```

<210> SEQ ID NO 13
<211> LENGTH: 21
<212> TYPE: DNA
<213> ORGANISM: Mus musculus
<220> FEATURE:
<221> NAME/KEY: misc_feature
<223> OTHER INFORMATION: CDR-H2 of murine anti-IL4 antibody

<400> SEQUENCE: 13

```
aaagtttcca accgattttc t                                                  21
```

<210> SEQ ID NO 14
<211> LENGTH: 27
<212> TYPE: DNA
<213> ORGANISM: Mus musculus
<220> FEATURE:
<221> NAME/KEY: misc_feature
<223> OTHER INFORMATION: CDR-H3 of murine anti-IL4 antibody

<400> SEQUENCE: 14

```
tttcaaggtt cacatgttcc gctcacg                                            27
```

<210> SEQ ID NO 15
<211> LENGTH: 336
<212> TYPE: DNA
<213> ORGANISM: Mus musculus
<220> FEATURE:
<221> NAME/KEY: misc_feature
<223> OTHER INFORMATION: LIGHT CHAIN of murine anti-IL4 antibody

<400> SEQUENCE: 15

```
gatgttttga tgacccaaac tccactctcc ctgcctgtcg gtcttggaga tcaagcctcc        60
atctcctgca gatctagtca gaccattgta catagtaatg aaagaccta tttagaatgg       120
tacctgcaga aaccaggcca gtctccaaag ctcctgatct acaaagtttc caaccgattt      180
tctggggtcc cagacaggtt cagtggcagt ggatcaggga cagatttcac actcaagatc      240
agcagagtgg aggctgagga tctgggagtt tattactgct ttcaaggttc acatgttccg      300
ctcacgttcg gtgctgggac caagctggag ctgaaa                                 336
```

<210> SEQ ID NO 16
<211> LENGTH: 342
<212> TYPE: DNA
<213> ORGANISM: Mus musculus
<220> FEATURE:
<221> NAME/KEY: misc_feature
<223> OTHER INFORMATION: HEAVY CHAIN of murine anti-IL4 antibody

<400> SEQUENCE: 16

```
gaggtccagc tgcaacagtt tggagctgag ctggtgaagc ctggggcttc agtgaagata        60
tcctgcaagg cttctggcta cacattcact gactacaaca tggactgggt gaagcagagc      120
```

-continued

```
catggaaaga gccttgagtg gattggagat attaatccta actatgaaag tactacctac      180
aaccagaagt tcaagggaaa ggccaccttg actgtagaca ggtcctccag cacagcctac      240
atggagctcc gcagcctgac atctgaggac actgcagtct attactgttt aagatccgga      300
ggtgactact ggggccaagg caccactctc acagtctcct ca                         342
```

ANTI IL-34 ANTIBODIES

CROSS-REFERENCE TO RELATED APPLICATIONS

This application is a U.S. National Stage Application pursuant to 35 U.S.C. § 371 of International Patent Application PCT/EP2015/080866, filed on Dec. 21, 2015, and published as WO 2016/097420 on Jun. 23, 2016, which claims priority to European Patent Application 14199494.7, filed on Dec. 19, 2014, all of which are incorporated herein by reference in their entireties for all purposes.

BACKGROUND OF THE INVENTION

The present invention relates to novel antibodies, in particular murine monoclonal antibodies, chimeric and humanized, able to bind specifically interleukin IL-34 as well as the amino and nucleic acid sequences coding for such antibodies. From one aspect, the invention relates to novel antibodies or an antigen fragments thereof, able to bind specifically to the IL-34. The invention also comprises the use of such antibodies or an antigen fragments thereof as a medicament for the preventive and/or therapeutic treatment of diseases involving IL-34.

In 2008, a new cytokine named interleukin-34 (IL-34) was discovered by Lin et al. based on its ability to induce the formation of colony-forming unit-macrophages in human bone marrow cultures, with the same efficiency as Macrophage Colony Stimulating Factor (M-CSF) (Lin et al., 2008). IL-34 bind in a close way to the extracellular domain of CSF-1 receptor (M-CSFR), but with a different binding mode of M-CSF (Felix et al., 2013; Ma et al., 2012) leading to receptor dimerization and differential autophosphorylation on its eight tyrosine residues.

More recently, Wang et al. reported that IL-34 was a specific driver of myeloid cell differentiation in the skin epidermis and central nervous system (Wang et al., 2012). IL-34 also directs the differentiation of monocytes into immunosuppressive M2 similar to M-CSF (Foucher et al., 2013). In addition, it was demonstrated, that IL-34 is expressed by giant cell tumours of bone and can be a substitute for M-CSF in promoting osteoclastogenesis (Baud'huin et al., 2010). IL-34, like M-CSF, upregulates the chemokines produced by whole blood, identifying both cytokines as key partners in inflammation (Eda et al., 2010). The role of IL-34 was also confirmed in rheumatoid arthritis.

Furthermore, IL-34 is involved in some cancers such as osteosarcoma, Ewing's sarcoma, bone tumors, brain cancer, in skin diseases and in metabolic diseases such as atherosclerosis (Ségaliny et al., 2014, Stanley et al., 2014, Wang et al., 2014 and Cronk et at., 2013). The majority of these effects of IL-34 are mediated by M-SFR. 11-34 also plays a singular role that has recently been explained in the brain through a binding to the receptor protein tyrosine phosphatase RPTPβ/ζ.

Thus, it is important to have means regulating the interaction between 11-34 and its receptor.

The use of monoclonal antibodies (mAbs) for cancer therapy has achieved considerable success in recent years. Such therapeutics function through mediating alterations in antigen or receptor function, modulating the immune system or delivering a specific drug that is conjugated to an antibody that targets a specific antigen.

A monoclonal antibody Rg7155 inhibiting CSF-1 receptor dimerization was previously described. The administration of this antibody to the patient led to striking reductions of CSF-1R$^+$CD163$^+$ macrophage infiltrations in tumor tissues, which translated into clinical objective responses in diffuse-type giant cell tumor patients (Ries et al., 2014).

However this antibody is nonspecific since it inhibits similarly both M-CSF and IL-34 binding.

An anti-IL-34 antibody is also described in WO 2013/119716. This antibody is capable of binding IL-34 and thus blocking the interaction between IL-34. This antibody is capable of binding of inhibiting the signalization pathway mediated from the binding of IL-34 to its receptor. Moreover, it is used in for treating some immunological diseases.

Furthermore, WO 2013/119716 discloses that said antibody anti-IL-34 has a binding affinity to its ligand IL-34 comprised between $1.7 \times 10^{-8}$ and $1.24 \times 10^{-10}$ which is said to seem to be a good affinity.

However, it is well known in the art that the strength of binding affinity of an antibody to its target is very important criteria for selecting therapeutically effective antibodies.

There is thus still a need for novel antibodies specifically targeting IL-34 and having a very strong binding activity for its target, which could be used for efficiently treating auto-immune diseases and cancer.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION

Surprisingly, the present inventors discovered an antibody specifically binding IL-34. Furthermore, the inventors demonstrated that the binding affinity of these antibodies for IL-34 is very high, in particular in comparison with the antibody anti-IL-34 disclosed in the prior art. As demonstrated in the examples of the present application, the binding affinity of the antibodies of the invention or the antigen binding fragments thereof is so high that it is difficult to determine its dissociation constant $K_D$ by conventional means.

These antibodies are able to block biological activities of IL-34 by inhibiting the interaction of 11-34 with M-CSFR. Indeed, IL-34-dependent cell proliferation is blocked by the antibodies of the invention. In addition, intra-cellular signal transduction triggered by IL-34 binding to its receptor is inhibited by the antibodies of the invention. In such manner, these antibodies are useful in the prevention and/or in the treatment of diseases involving IL-34, including e.g. inflammatory diseases, cancer, bone disease, skin diseases, metabolic diseases, cerebral diseases and hepatic diseases and auto-immune diseases.

In a first aspect, the antibodies of the invention or antigen-binding fragments thereof, comprise a light chain comprising three CDRs of the sequences SEQ ID Nos.1, 2 or 3, or at least one sequence with at least 80%, preferably 85%, 90%, 95% and 98% identity after optimal alignment with sequences SEQ ID Nos.1, 2 or 3 and three CDRs of the sequences SEQ ID Nos. 4, 5 or 6, or at least one sequence with at least 80%, preferably 85%, 90%, 95% and 98% identity after optimal alignment with sequences SEQ ID Nos. 4, 5 or 6.

As used herein, the "percentage identity" between two sequences of nucleic acids or amino acids means the percentage of identical nucleotides or amino acid residues between the two sequences to be compared, obtained after optimal alignment, this percentage being purely statistical and the differences between the two sequences being distributed randomly along their length. The comparison of two nucleic acid or amino acid sequences is traditionally carried out by comparing the sequences after having optimally aligned them, said comparison being able to be conducted by segment or by using an "alignment window". Optimal alignment of the sequences for comparison can be carried out, in addition to comparison by hand, by means of the local homology algorithm of Smith and Waterman (1981) [Ad. App. Math. 2:482], by means of the local homology algorithm of Neddleman (1970) [J. Mol. Biol. 48:443], by means of the similarity search method of Pearson (1988) [Proc. Natl. Acad. Sci. USA 85:2444] or by means of computer software using these algorithms (GAP, BESTFIT, FASTA and TFASTA in the Wisconsin Genetics Software Package, Genetics Computer Group, 575 Science Dr., Madison, Wis., or by the comparison software BLAST NR or BLAST P).

The percentage identity between two nucleic acid or amino acid sequences is determined by comparing the two optimally-aligned sequences in which the nucleic acid or amino acid sequence to compare can have additions or deletions compared to the reference sequence for optimal alignment between the two sequences. Percentage identity is calculated by determining the number of positions at which the amino acid nucleotide or residue is identical between the two sequences, preferably between the two complete sequences, dividing the number of identical positions by the total number of positions in the alignment window and multiplying the result by 100 to obtain the percentage identity between the two sequences.

For example, the BLAST program, "BLAST 2 sequences" (Tatusova et al., "Blast 2 sequences—a new tool for comparing protein and nucleotide sequences", FEMS Microbiol. Lett. 1999, 174:247-250) can be used with the default parameters (notably for the parameters "open gap penalty": 5, and "extension gap penalty": 2; the selected matrix being for example the "BLOSUM 62" matrix proposed by the program); the percentage identity between the two sequences to compare is calculated directly by the program.

For the amino acid sequence exhibiting at least 80%, preferably 85%, 90%, 95% and 98% identity with a reference amino acid sequence, preferred examples include those containing the reference sequence, certain modifications, notably a deletion, addition or substitution of at least one amino acid, truncation or extension. In the case of substitution of one or more consecutive or non-consecutive amino acids, substitutions are preferred in which the substituted amino acids are replaced by "equivalent" amino acids. Here, the expression "equivalent amino acids" is meant to indicate any amino acids likely to be substituted for one of the structural amino acids without however modifying the biological activities of the corresponding antibodies and of those specific examples defined below.

Equivalent amino acids can be determined either on their structural homology with the amino acids for which they are substituted or on the results of comparative tests of biological activity between the various antibodies likely to be generated.

As a non-limiting example, table 1 below summarizes the possible substitutions likely to be carried out without resulting in a significant modification of the biological activity of the corresponding modified antibody; inverse substitutions are naturally possible under the same conditions.

TABLE 1

| Original residue | Substitution(s) |
|---|---|
| Ala (A) | Val, Gly, Pro |
| Arg (R) | Lys, His |
| Asn (N) | Gln |
| Asp (D) | Glu |
| Cys (C) | Ser |
| Gln (Q) | Asn |
| Glu (G) | Asp |
| Gly (G) | Ala |
| His (H) | Arg |
| Ile (I) | Leu |
| Leu (L) | Ile, Val, Met |
| Lys (K) | Arg |
| Met (M) | Leu |
| Phe (F) | Tyr |
| Pro (P) | Ala |
| Ser (S) | Thr, Cys |
| Thr (T) | Ser |
| Trp (W) | Tyr |
| Tyr (Y) | Phe, Trp |
| Val (V) | Leu, Ala |

In a first embodiment, the anti-IL-34 antibodies of the invention or antigen-binding fragments thereof comprise a light chain comprising CDR-L1, CDR-L2 and CDR-L3 comprising respectively the amino acid sequence SEQ ID Nos. 1, 2 and 3; and a heavy chain comprising CDR-H1, CDR-H2 and CDR-H3 comprising respectively the amino acid sequence SEQ ID Nos. 4, 5 and 6.

In another embodiment, the anti-IL-34 antibodies of the invention or antigen-binding fragments thereof comprise a light chain comprising CDR-L1, CDR-L2 and CDR-L3 having respectively the amino acid sequence SEQ ID Nos. 1, 2 and 3; and a heavy chain comprising CDR-H1, CDR-H2 and CDR-H3 having respectively the amino acid sequence SEQ ID Nos. 4, 5 and 6.

The term "antibody" is used herein in the broadest sense and specifically covers monoclonal antibodies (including full length monoclonal antibodies) of any isotype such as IgG, IgM, IgA, IgD, and IgE, polyclonal antibodies, multi-specific antibodies, chimeric antibodies, and antigen-binding fragments. An antibody reactive with a specific antigen can be generated by recombinant methods such as selection of libraries of recombinant antibodies in phage or similar vectors, or by immunizing an animal with the antigen or an antigen-encoding nucleic acid.

A typical antibody is comprised of two identical light chains and two identical heavy chains that are joined by disulfide bonds.

As used in the invention, the term "light chain" refers to mammalian immunoglobulin light chain, lambda (λ) or kappa (κ), having two successive domains: one constant domain and one variable domain.

As used in the invention, the term "heavy chain" refers to chain of mammalian immunoglobulin denoted by: α, δ, ε, γ, and μ. Each heavy chain has two regions, the constant region and the variable region. The constant region is identical in all antibodies of the same isotype. The variable region of each heavy chain is composed of a single Ig domain.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

Each variable region contains three segments called "complementarity-determining regions" ("CDRs") or "hypervariable regions", which are primarily responsible for binding an epitope of an antigen. The CDRs thus direct the specificity of the binding of the antibody. They are usually referred to as CDR1, CDR2, and CDR3, numbered sequentially from the N-terminus. The most highly conserved portions of the variable regions are called the "framework regions".

In one embodiment, the antibody of the invention, or antigen-binding fragments thereof, comprises a light chain variable domain of sequence comprising the amino acid sequence SEQ ID No. 7, or at least one sequence with at least 80%, preferably 85%, 90%, 95% and 98% identity after optimal alignment with sequences SEQ ID No. 7 and a heavy chain variable domain of sequence comprising the amino acid sequence SEQ ID No. 8, or at least one sequence with at least 80%, preferably 85%, 90%, 95% and 98% identity after optimal alignment with sequences SEQ ID No. 8.

In preferred embodiment, the antibodies of the invention, or an antigen binding fragment thereof, comprise a light chain comprising the amino acid sequence SEQ ID No. 7 and a heavy chain comprising the amino acid sequence SEQ ID No. 8.

In another preferred embodiment, the antibodies of the invention, or an antigen binding fragment thereof, comprise a light chain having the amino acid sequence SEQ ID No. 7 and a heavy chain having the amino acid sequence SEQ ID No. 8.

According to the present invention, the sequences corresponding to complete variable chains of said antibodies and of their CDR were analyzed on the IgBlast database to identify the CDRs.

IgBlast database was developed to analyse nucleotide and protein sequences and can process sequences in batches. Furthermore, IgBLAST allows searches against the germline gene databases and other sequence databases simultaneously to minimize the chance of missing possibly the best matching germline V gene (variable gene of immunoglobulin). Further information about IgBLAST database is herewith included by reference to Ye et al. *"IgBLAST: an immunoglobulin variable domain sequence analysis tool"*, published on Jun. 22, 2013 on the website of Oxford Journal.

In one embodiment, the present application relates to polyclonal antibodies.

A "polyclonal antibody" is an antibody which was produced among or in the presence of one or more other, non-identical antibodies. In general, polyclonal antibodies are produced from a B-lymphocyte in the presence of several other B-lymphocytes producing non-identical antibodies. Usually, polyclonal antibodies are obtained directly from an immunized animal.

According to another embodiment, the antibody of the invention, or antigen-binding fragments thereof, is a monoclonal antibody. In a specific embodiment, the present invention relates to murine monoclonal antibodies, or antigen-binding fragments thereof.

As used herein, the term "monoclonal antibody" refers to an antibody arising from a nearly homogeneous antibody population. More particularly, the individual antibodies of a population are identical except for a few possible naturally-occurring mutations which can be found in minimal proportions. In other words, a monoclonal antibody consists of a homogeneous antibody population arising from the growth of a single cell clone (for example a hybridoma, a eukaryotic host cell transfected with a DNA molecule coding for the homogeneous antibody, a prokaryotic host cell transfected with a DNA molecule coding for the homogeneous antibody, etc.) and is generally characterized by heavy chains of one and only one class and subclass, and light chains of only one type. Monoclonal antibodies are highly specific and are directed against a single antigen.

An "antigen" is a predetermined molecule to which an antibody can selectively bind. The target antigen may be a polypeptide, a carbohydrate, a nucleic acid, a lipid, a hapten or any other naturally occurring or synthetic compound. Preferably, the target antigen is a polypeptide.

An "epitope" is the site on the antigen to which an antibody specifically binds. It can be formed by contiguous residues or by non-contiguous residues brought into close proximity by the folding of an antigenic protein. Epitopes formed by contiguous amino acids are typically retained on exposure to denaturing solvents, whereas epitopes formed by non-contiguous amino acids are typically lost under said exposure.

In one embodiment, the invention provides antibodies or antigen-binding fragments thereof capable of inhibiting the interaction of IL-34 with its receptors by binding IL-34 before the binding of IL-34 to its receptor.

In another embodiment, the invention provides antibodies or antigen-binding fragments thereof capable of inhibiting the interaction of IL-34 with its receptors by binding IL-34 after the binding of IL-34 to its receptor.

In yet another embodiment, the invention provides antibodies or antigen-binding fragments thereof capable of inhibiting the interaction of IL-34 with its receptors by binding IL-34 before and after the binding of IL-34 to its receptor.

Specifically, the antibodies or antigen-binding fragments thereof of the invention are capable of inhibiting the interaction of IL-34 with M-CSFR and/or RPTPBβ/ζ receptors.

In one embodiment, the invention provides antibodies or antigen-binding fragments thereof capable of inhibiting the interaction of IL-34 with M-CSFR and/or RPTPBβ/ζ receptors by binding IL-34 before the binding of IL-34 to M-CSFR and/or RPTPBβ/ζ receptor.

In another embodiment, the invention provides antibodies or antigen-binding fragments thereof capable of inhibiting the interaction of IL-34 with M-CSFR and/or RPTPBβ/ζ receptors by binding IL-34 after the binding of IL-34 to M-CSFR and/or RPTPBβ/ζ receptor.

In yet another embodiment, the invention provides antibodies or antigen-binding fragments thereof capable of inhibiting the interaction of IL-34 with M-CSFR and/or RPTPBβ/ζ receptors by binding IL-34 before and after the binding of IL-34 to M-CSFR and/or RPTPBβ/ζ receptor.

The antibodies of the invention are thus capable of inhibiting IL-34-mediated signalization. This is particularly useful, since IL-34 has been shown to be involved in the development of a number of pathologies, including e.g. inflammatory diseases, cancer, bone disease, skin diseases, metabolic diseases, cerebral diseases and hepatic diseases and auto-immune diseases.

The inventors demonstrated that the antibodies of the present invention have a high affinity for IL-34. This is correlated with the very low dissociation constant ($K_D$) which was difficult to measure by the inventors using conventional means.

Preferably, the antibody or antigen-binding fragments thereof have a dissociation constant ($K_D$) $K_D \leq 10^{-11}$·M. More preferably the antibody or antigen-binding fragments thereof have a dissociation constant $K_D \leq 9.4 \pm 0.7 \times 10^{-12}$M measured by BIAcore.

As used herein, the term "$K_D$" refers to the dissociation constant of a particular antibody/antigen interaction.

As used herein the term "binding affinity" or "affinity of binding" generally refers to the strength of the sum total of noncovalent interactions between a single binding site of a molecule (e.g., an antibody or antigen binding fragments thereof) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

As used herein, the term "BIACore" relates to a technology based on surface plasmon resonance (SPR), an optical phenomenon that enables detection of unlabeled interactants in real time. BIACore technology involves immobilizing one molecule of a binding pair on the sensor chip surface ("ligand", in Biacore parlance) and injecting a series of concentrations of its partner ("analyte") across the surface. Changes in the index of refraction at the surface where the binding interaction occurs are detected by the hardware and recorded as RU (resonance units) in the control software. Curves are generated from the RU trace and are evaluated by fitting algorithms which compare the raw data to well-defined binding models. These fits allow determination of apparent affinity of the binding interaction.

It must be understood here that the invention does not relate to antibodies in natural form, i.e., they are not taken from their natural environment but are isolated or obtained by purification from natural sources or obtained by genetic recombination or chemical synthesis and thus they can carry unnatural amino acids as will be described below.

In another aspect, the invention relates to chimeric or humanized antibodies, or antigen-binding fragments thereof, which can be obtained by genetic engineering or by chemical synthesis.

Specifically, the anti-IL-34 antibodies of the invention are chimeric antibodies.

The term "chimeric antibody" as used herein refers to an antibody containing a natural variable region (light chain and heavy chain) derived from an antibody of a given species in combination with constant regions of the light chain and the heavy chain of an antibody of a species heterologous to said given species. Thus, a "chimeric antibody", as used herein, is an antibody in which the constant region, or a portion thereof, is altered, replaced, or exchanged, so that the variable region is linked to a constant region of a different species, or belonging to another antibody class or subclass. "Chimeric antibody" also refers to an antibody in which the variable region, or a portion thereof, is altered, replaced, or exchanged, so that the constant region is linked to a variable region of a different species, or belonging to another antibody class or subclass.

The antibodies, or chimeric fragments of same, can be prepared by recombinant engineering. For example, the chimeric antibody could be produced by cloning recombinant DNA containing a promoter and a sequence coding for the variable region of a nonhuman monoclonal antibody of the invention, notably murine, and a sequence coding for the human antibody constant region. A chimeric antibody according to the invention coded by one such recombinant gene could be, for example, a mouse-human chimera, the specificity of this antibody being determined by the variable region derived from the murine DNA and its isotype determined by the constant region derived from human DNA. Refer to Verhoeyn et al. (BioEssays, 8:74, 1988) for methods for preparing chimeric antibodies.

Preferably, the invention relates to a chimeric antibody, or antigen binding fragments thereof, comprising a light chain comprising CDR-L1, CDR-L2 and CDR-L3 comprising respectively the amino acid sequence SEQ ID Nos. 1, 2 and 3; and a heavy chain comprising CDR-H1, CDR-H2 and CDR-H3 comprising respectively the amino acid sequence SEQ ID Nos. 4, 5 and 6.

More preferably, the chimeric antibody of the invention, or antigen binding fragments thereof, comprises a light chain having CDR-L1, CDR-L2 and CDR-L3 having respectively the amino acid sequence SEQ ID Nos. 1, 2 and 3; and a heavy chain comprising CDR-H1, CDR-H2 and CDR-H3 having respectively the amino acid sequence SEQ ID Nos. 4, 5 and 6.

In another embodiment, the invention relates to a chimeric antibody, or antigen-binding fragments thereof, comprising a light chain variable region of sequence SEQ ID No. 7 and a heavy chain variable region of sequence consisting of SEQ ID No. 8.

In more preferred embodiment of the invention, the chimeric antibody is an antibody comprising the constant regions from human and the variable regions from mouse.

The skilled artisan will be capable to adapt the conventional methods for obtaining chimeric antibodies as cited above in order to produce the chimeric antibodies according to the invention.

In another aspect, the present invention provides humanized anti-IL-34 antibodies, or antigen-binding fragments thereof.

As used herein, the term "humanized antibody" refers to a chimeric antibody which contain minimal sequence derived from non-human immunoglobulin. In one embodiment, a humanized antibody is a human immunoglobulin (recipient antibody) in which residues from a CDR of the recipient are replaced by residues from a CDR of a non-human species (donor antibody) such as mouse, rat, rabbit or non-human primate having the desired specificity, affinity, and/or capacity. In some instances, framework ("FR") residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR are typically no more than 6 in the H chain, and in the L chain, no more than 3. The humanized antibody optionally will also comprise at least a portion of an immunoglobulin constant region (Fc), typically that of a human immunoglobulin.

The goal of humanization is a reduction in the immunogenicity of a xenogenic antibody, such as a murine antibody, for introduction into a human, while maintaining the full antigen binding affinity and specificity of the antibody. Humanized antibodies, or antibodies adapted for non-rejection by other mammals, may be produced using several technologies such as resurfacing and CDR grafting. As used herein, the resurfacing technology uses a combination of molecular modeling, statistical analysis and mutagenesis to alter the non-CDR surfaces of antibody variable regions to resemble the surfaces of known antibodies of the target host.

Strategies and methods for the resurfacing of antibodies, and other methods for reducing immunogenicity of antibodies within a different host, are disclosed in U.S. Pat. No. 5,639,641, which is hereby incorporated in its entirety by reference. Briefly, in a preferred method, (1) position alignments of a pool of antibody heavy and light chain variable regions is generated to give a set of heavy and light chain variable region framework surface exposed positions wherein the alignment positions for all variable regions are at least about 98% identical; (2) a set of heavy and light chain variable region framework surface exposed amino acid residues is defined for a rodent antibody (or fragment thereof); (3) a set of heavy and light chain variable region framework surface exposed amino acid residues that is most closely identical to the set of rodent surface exposed amino acid residues is identified; (4) the set of heavy and light chain variable region framework surface exposed amino acid residues defined in step (2) is substituted with the set of heavy and light chain variable region framework surface exposed amino acid residues identified in step (3), except for those amino acid residues that are within 5 A of any atom of any residue of the complementarity-determining regions of the rodent antibody; and (5) the humanized rodent antibody having binding specificity is produced.

Antibodies can be humanized using a variety of other techniques including CDR-grafting (EP 0 239 400; WO 91/09967; U.S. Pat. Nos. 5,530,101; and 5,585,089), veneering or resurfacing (EP 0 592 106; EP 0 519 596; Padlan E. A., 1991, Molecular Immunology 28(4/5): 489-498; Studnicka G. M. et al., 1994, Protein Engineering 7(6): 805-814; Roguska M. A. et al., 1994, Proc. Natl. Acad. ScL U.S.A., 91:969-973), and chain shuffling (U.S. Pat. No. 5,565,332). Human antibodies can be made by a variety of methods known in the art including phage display methods. See also U.S. Pat. Nos. 4,444,887, 4,716,111, 5,545,806, and 5,814,318; and international patent application publication numbers WO 98/46645, WO 98/50433, WO 98/24893, WO 98/16654, WO 96/34096, WO 96/33735, and WO 91/10741 (said references incorporated by reference in their entireties).

According to the invention the humanized antibodies arise from the murine antibody described above.

More particularly, the invention relates to a humanized antibody, or antigen-binding fragments thereof, comprising a light chain comprising CDR-L1, CDR-L2 and CDR-L3 comprising respectively the amino acid sequence SEQ ID Nos. 1, 2 and 3; and a heavy chain comprising CDR-H1, CDR-H2 and CDR-H3 comprising respectively the amino acid sequence SEQ ID Nos. 4, 5 and 6.

Still more particularly, the invention relates to a humanized antibody, or antigen-binding fragments thereof, comprising a light chain comprising CDR-L1, CDR-L2 and CDR-L3 having respectively the amino acid sequence SEQ ID Nos. 1, 2 and 3; and a heavy chain comprising CDR-H1, CDR-H2 and CDR-H3 having respectively the amino acid sequence SEQ ID Nos. 4, 5 and 6.

Thus, in a specific embodiment, the present invention provides humanized antibodies or antigen-binding fragments thereof, which specifically bind IL-34 ant thus inhibit the interaction between IL-34 and its receptors.

Another aspect of the invention relates to the antigen-binding fragments of the antibody described above.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10): 1057-1062 [1995]); single-chain antibody molecules and multispecific antibodies formed from antibody fragments. Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The term "Fv" as used herein refers to the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in *The Pharmacology of Monoclonal Antibodies*, vol. 113, Rosenburg and Moore eds., Springer-Verlag, New York, pp. 269-315 (1994).

"Functional fragments" of the antibodies of the invention comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Natl. Acad. Sci. USA* 90: 6444-6448 (1993).

More particularly, the invention provides an anti-IL-34 antibody, or its derived compounds or functional fragments, characterized in that said functional fragment is selected among the fragments Fv, Fab, (Fab')$_2$, Fab', scFv, scFv-Fc and diabodies, or any fragment whose half-life has been increased by chemical modification.

The chemical modification as cited above, may be such as the addition of polyalkylene glycol such as polyethylene glycol (PEGylation) (PEGylated fragments are referred to as Fv-PEG, scFv-PEG, Fab-PEG, F(ab')$_2$-PEG and Fab'-PEG), or by incorporation in a liposome, microspheres or PLGA, said fragments possessing at least six of CDRs of the invention which is notably capable of exerting in a general manner activity, even partial, of the antibody from which it arises.

Preferably, said antigen-binding fragment will comprise or include a partial sequence of the variable heavy or light chain of the antibody from which they are derived, said partial sequence being sufficient to retain the same binding specificity as the antibody from which it arises and sufficient affinity, preferably at least equal to $\frac{1}{100}$, more preferably at least $\frac{1}{10}$ of that of the antibody from which it arises.

Preferably, this antigen-binding fragment will be of the types Fv, scFv, Fab, F(ab')$_2$, F(ab'), scFv-Fc or diabodies, which generally have the same binding specificity as the antibody from which they result.

According to the present invention, antigen-binding fragments of the invention can be obtained from the antibodies described above by methods such as enzyme digestion, including pepsin or papain, and/or by cleavage of the disulfide bridges by chemical reduction. The antigens-binding fragments can be also obtained by recombinant genetics techniques also known to a person skilled in the art or by peptide synthesis by means, for example, of automatic peptide synthesizers such as those sold by Applied BioSystems, etc.

A novel aspect of the present invention relates to an isolated nucleic acid characterized in that it is selected among the following nucleic acids (including any degenerate genetic code):

a) a nucleic acid, DNA or RNA, coding for an antibody, or one of its functional fragments or derivatives, according to the invention;

b) a nucleic acid comprising a DNA sequence selecting from the group of sequences consisting of SEQ ID Nos. 9 to 14;

c) a nucleic acid comprising a DNA sequence selecting from the group of sequences consisting of SEQ ID Nos. 15 and 16.

In a specific embodiment, the invention is directed to six polynucleotides of the invention, wherein each polynucleotide encodes a specific CDR of the antibody of the invention.

In a specific embodiment, the invention is directed to a pair of polynucleotides of the invention, wherein one of the polynucleotides encodes the heavy chain and the other polynucleotide encodes the light chain of an antibody of the invention.

The terms "nucleic acid", "nucleic sequence", "nucleic acid sequence", "polynucleotide", "oligonucleotide", "polynucleotide sequence" and "nucleotide sequence", used interchangeably in the present description, mean a precise sequence of nucleotides, modified or not, defining a fragment or a region of a nucleic acid, containing unnatural nucleotides or not, and being either a double-strand DNA, a single-strand DNA or transcription products of said DNAs.

It should also be included here that the present invention does not relate to nucleotide sequences in their natural chromosomal environment, i.e., in a natural state. The sequences of the present invention have been isolated and/or purified, i.e., they were sampled directly or indirectly, for example by a copy, their environment having been at least partially modified. Isolated nucleic acids obtained by recombinant genetics, by means, for example, of host cells, or obtained by chemical synthesis should also be mentioned here.

"Nucleic sequences exhibiting a percentage identity of at least 80%, preferably 85%, 90%, 95% and 98%, after optimal alignment with a preferred sequence" means nucleic sequences exhibiting, with respect to the reference nucleic sequence, certain modifications such as, in particular, a deletion, a truncation, an extension, a chimeric fusion and/or a substitution, notably punctual. Preferably, these are sequences which code for the same amino acid sequences as the reference sequence, this being related to the degeneration of the genetic code, or complementarity sequences that are likely to hybridize specifically with the reference sequences, preferably under highly stringent conditions, notably those defined below.

Hybridization under highly stringent conditions means that conditions related to temperature and ionic strength are selected in such a way that they allow hybridization to be maintained between two complementarity DNA fragments. On a purely illustrative basis, the highly stringent conditions of the hybridization step for the purpose of defining the polynucleotide fragments described above are advantageously as follows.

DNA-DNA or DNA-RNA hybridization is carried out in two steps: (1) prehybridization at 42° C. for three hours in phosphate buffer (20 mM, pH 7.5) containing 5×SSC (1×SSC corresponds to a solution of 0.15 M NaCl+0.015 M sodium citrate), 50% formamide, 7% sodium dodecyl sulfate (SDS), 10×Denhardt's, 5% dextran sulfate and 1% salmon sperm DNA; (2) primary hybridization for 20 hours at a temperature depending on the length of the probe (i.e.: 42° C. for a probe >100 nucleotides in length) followed by two 20-minute washings at 20° C. in 2×SSC+2% SDS, one 20-minute washing at 20° C. in 0.1×SSC+0.1% SDS. The last washing is carried out in 0.1×SSC+0.1% SDS for 30 minutes at 60° C. for a probe >100 nucleotides in length. The highly stringent hybridization conditions described above for a polynucleotide of defined size can be adapted by a person skilled in the art for longer or shorter oligonucleotides, according to the procedures described in Sambrook, et al. (Molecular cloning: a laboratory manual, Cold Spring Harbor Laboratory; 3rd edition, 2001).

According to the invention, a variety of expression systems may be used to express the IgG antibody of the invention. In one aspect, such expression systems represent vehicles by which the coding sequences of interest may be produced and subsequently purified, but also represent cells which may, when transiently transfected with the appropriate nucleotide coding sequences, express an IgG antibody of the invention in situ.

The invention provides vectors comprising the polynucleotides of the invention. In one embodiment, the vector contains a polynucleotide encoding a heavy chain of an anti-Il-34 antibody of the invention, i.e. an antibody which carries a mutation in the Fc domain. In another embodiment, said polynucleotide encodes the light chain of an IgG antibody of the invention. The invention also provides vectors comprising polynucleotide molecules encoding fusion proteins, modified antibodies, antibody fragments, and probes thereof.

In order to express the heavy and/or light chain of the anti-IL-34 antibody of the invention, the polynucleotides encoding said heavy and/or light chains are inserted into expression vectors such that the genes are operatively linked to transcriptional and translational sequences.

"Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e. g., bacterial vectors having a bacterial origin of replication and episomal mammalian vectors). Other vectors (e. g., non-episomal mammalian vectors) can be integrated into the genome of a host cell upon introduction into the host cell, and thereby are replicated along with the host genome.

Certain vectors are capable of directing the expression of genes to which they are operatively linked. Such vectors are referred to herein as "recombinant expression vectors" (or simply, "expression vectors"). In general, expression vectors of utility in recombinant DNA techniques are in the form of plasmids. In the present specification, "plasmid" and "vector" may be used interchangeably as the plasmid is the most commonly used form of vector. However, the invention is intended to include such forms of expression vectors, such as bacterial plasmids, YACs, cosmids, retrovirus, EBV-derived episomes, and all the other vectors that the skilled man will know to be convenient for ensuring the expression of the heavy and/or light chains of the antibodies of the invention. The skilled man will realize that the polynucleotides encoding the heavy and the light chains can be cloned into different vectors or in the same vector. In a preferred embodiment, said polynucleotides are cloned into two vectors.

Polynucleotides of the invention and vectors comprising these molecules can be used for the transformation of a suitable host cell. The term "host cell", as used herein, is intended to refer to a cell into which a recombinant expression vector has been introduced in order to express the IgG antibody of the invention. It should be understood that such terms are intended to refer not only to the particular subject cell but also to the progeny of such a cell. Because certain modifications may occur in succeeding generations due to either mutation or environmental influences, such progeny may not, in fact, be identical to the parent cell, but are still included within the scope of the term "host cell" as used herein.

Transformation can be performed by any known method for introducing polynucleotides into a cell host. Such methods are well known of the man skilled in the art and include dextran-mediated transformation, calcium phosphate precipitation, polybrene-mediated transfection, protoplast fusion, electroporation, encapsulation of the polynucleotide into liposomes, biolistic injection and direct microinjection of DNA into nuclei.

The host cell may be co-transfected with two or more expression vectors, including the vector expressing the protein of the invention. For example, a host cell can be transfected with a first vector encoding an IgG antibody, as described above, and a second vector encoding a glycosyltransferase polypeptide. Alternatively, the host cell can be transformed with a first vector encoding an antibody of the invention, a second vector encoding a glycosyltransferase, as described above, and a third vector encoding another glycosyltransferase. Mammalian cells are commonly used for the expression of a recombinant therapeutic immunoglobulins, especially for the expression of whole recombinant anti-IL-34 antibodies. For example, mammalian cells such as HEK293 or CHO cells, in conjunction with a vector, containing the expression signal such as one carrying the major intermediate early gene promoter element from human cytomegalovirus, are an effective system for expressing the IgG antibody of the invention (Foecking et al., 1986, Gene 45:101; Cockett et al., 1990, Bio/Technology 8:2).

In addition, a host cell is chosen which modulates the expression of the inserted sequences, or modifies and processes the gene product in the specific fashion desired. Such modifications (e.g., glycosylation) and processing of protein products may be important for the function of the protein. Different host cells have features and specific mechanisms for the post-translational processing and modification of proteins and gene products. Appropriate cell lines or host systems are chosen to ensure the correct modification and processing of the expressed antibody of interest. Hence, eukaryotic host cells which possess the cellular machinery for proper processing of the primary transcript, glycosylation of the gene product may be used. Such mammalian host cells include, but are not limited to, CHO, COS, HEK293, NS/0, BHK, Y2/0, 3T3 or myeloma cells (all these cell lines are available from public deposiceries such as the Collection Nationale des Cultures de Microorganismes, Paris, France, or the American Type Culture Collection, Manassas, Va., U.S.A.).

For long-term, high-yield production of recombinant proteins, stable expression is preferred. In one embodiment of the invention, cell lines which stably express the antibody may be engineered. Rather than using expression vectors which contain viral origins of replication, host cells are transformed with DNA under the control of the appropriate expression regulatory elements, including promoters, enhancers, transcription terminators, polyadenylation sites, and other appropriate sequences known to the person skilled in art, and a selectable marker. Following the introduction of the foreign DNA, engineered cells may be allowed to grow for one to two days in an enriched media, and then are moved to a selective media. The selectable marker on the recombinant plasmid confers resistance to the selection and allows cells to stably integrate the plasmid into a chromosome and be expanded into a cell line. Other methods for constructing stable cell lines are known in the art. In particular, methods for site-specific integration have been developed. According to these methods, the transformed DNA under the control of the appropriate expression regulatory elements, including promoters, enhancers, transcription terminators, polyadenylation sites, and other appropriate sequences is integrated in the host cell genome at a specific target site which has previously been cleaved (Moele et al., Proc. Natl. Acad. Sci. U.S.A., 104(9): 3055-3060; U.S. Pat. Nos. 5,792,632; 5,830,729; 6,238,924; WO 2009/054985; WO 03/025183; WO 2004/067753).

A number of selection systems may be used according to the invention, including but not limited to the Herpes simplex virus thymidine kinase (Wigler et al., Cell 11:223, 1977), hypoxanthine-guanine phosphoribosyltransferase (Szybalska et al., Proc Natl Acad Sci USA 48: 202, 1992), glutamate synthase selection in the presence of methionine sulfoximide (Adv Drug Del Rev, 58: 671, 2006, and website or literature of Lonza Group Ltd.) and adenine phosphoribosyltransferase (Lowy et al., Cell 22: 817, 1980) genes in tk, hgprt or aprt cells, respectively. Also, antimetabolite resistance can be used as the basis of selection for the following genes: dhfr, which confers resistance to methotrexate (Wigler et al., Proc Natl Acad Sci USA 77: 357, 1980); gpt, which confers resistance to mycophenolic acid (Mulligan et al., Proc Natl Acad Sci USA 78: 2072, 1981); neo, which confers resistance to the aminoglycoside, G-418 (Wu et al., Biotherapy 3: 87, 1991); and hygro, which confers resistance to hygromycin (Santerre et al., Gene 30: 147, 1984). Methods known in the art of recombinant DNA technology may be routinely applied to select the desired recombinant clone, and such methods are described, for example, in Ausubel et al., eds., Current Protocols in Molecular Biology, John Wiley Et Sons (1993). The expression levels of an antibody can be increased by vector amplification. When a marker in the vector system expressing an antibody is amplifiable, an increase in the level of inhibitor present in the culture will increase the number of copies of the marker gene. Since the amplified region is associated with the gene encoding the IgG antibody of the invention, production of said antibody will also increase (Crouse et al., Mol Cell Biol 3: 257, 1983). Alternative methods of expressing the gene of the invention exist and are known to the person of skills in the art. For example, a modified zinc finger protein can be engineered that is capable of binding the expression regulatory elements upstream of the gene of the invention; expression of the said engineered zinc finger protein (ZFN) in the host cell of the invention leads to increases in protein production (see e. g. Reik et al., Biotechnol. Bioeng., 97(5), 1180-1189, 2006). Moreover, ZFN can stimulate the integration of a DNA into a predetermined genomic location, resulting in high-efficiency site-specifique gene addition (Moehle et al, PNAS 104, pp 3055, 2007).

The antibody of the invention may be prepared by growing a culture of the transformed host cells under culture conditions necessary to express the desired antibody. The resulting expressed antibody may then be purified from the culture medium or cell extracts. Soluble forms of the antibody of the invention can be recovered from the culture supernatant. It may then be purified by any method known in the art for purification of an immunoglobulin molecule, for example, by chromatography (e.g., ion exchange, affinity, particularly by Protein A affinity for Fc, and so on), centrifugation, differential solubility or by any other standard technique for the purification of proteins. Suitable methods of purification will be apparent to a person of ordinary skills in the art.

Another aspect of the invention thus relates to a method for the production of an antibody according to the invention, or antigen-binding fragments thereof, characterized in that said method comprises the following steps:

a) growing a host cell of the invention in an appropriate culture medium and b) recovering said antibody.

As mentioned above, the antibodies of the present invention bind specifically IL-34 with a very high affinity. In addition, they are capable of inhibiting IL-34-mediated cell proliferation and intracellular signal transduction. The antibodies of the invention are therefore particularly advantageous for the prevention and/or the treatment of various diseases involving IL-34 since they can prevent undesired activation of IL-34-dependent cellular signaling pathways. Moreover, since the antibodies of the invention are capable binding IL-34 with very high affinity before and/or after IL-34 binding to its receptor, the therapeutically efficiency of these antibody is increased.

As used herein, the terms "treat," treating," "treatment," and the like refer to reducing or ameliorating the symptoms of a disorder (e.g., an IL-34-related disorder) and/or symptoms associated therewith. It will be appreciated that, although not precluded, treating a disorder or condition does not require that the disorder, condition or symptoms associated therewith be completely eliminated.

As used herein "treating" a disease in a subject or "treating" a subject having a disease refers to subjecting the subject to a pharmaceutical treatment, e.g., the administration of a drug, such that the extent of the disease is decreased or prevented. For example, treating results in the reduction of at least one sign or symptom of the disease or condition. Treatment includes (but is not limited to) administration of a composition, such as a pharmaceutical composition, and may be performed either prophylactically, or subsequent to the initiation of a pathologic event. Treatment can require administration of an agent and/or treatment more than once.

A "subject" which may be subjected to said treatment described herein may be any of mammalian animals including human, dog, cat, cattle, goat, pig, swine, sheep and monkey. A human subject can be known as a patient. In one embodiment, "subject" or "patient" refers to a mammal affected by a disorder characterized by inappropriate activation of the IL-34 signaling pathway, e.g. through hyperactivation or deregulation. A "control subject" refers to a mammal wherein the IL-34 signaling pathway is correctly activated and regulated.

In another aspect, the invention relates to a pharmaceutical composition comprising an antibody of the invention, or antigen-binding fragments thereof. Preferably, the pharmaceutical composition of the invention may contain, in addition to the antibody of the invention, various diluents, fillers, salts, buffers, stabilizers, solubilizers, and other materials well known in the art.

As used herein, "pharmaceutically acceptable carrier" includes any and all solvents, buffers, salt solutions, dispersion media, coatings, antibacterial and antifungal agents, isotonic and absorption delaying agents, and the like that are physiologically compatible. The type of carrier can be selected based upon the intended route of administration. In various embodiments, the carrier is suitable for intravenous, intraperitoneal, subcutaneous, intramuscular, topical, transdermal or oral administration. Pharmaceutically acceptable carriers include sterile aqueous solutions or dispersions and sterile powders for the extemporaneous preparation of sterile injectable solutions or dispersion. The use of media and agents for pharmaceutically active substances is well known in the art. A typical pharmaceutical composition for intravenous infusion could be made up to contain 250 ml of sterile Ringer's solution, and 100 mg of the combination. Actual methods for preparing parenterally administrable compounds will be known or apparent to those skilled in the art and are described in more detail in for example, Remington's Pharmaceutical Science, 17th ed., Mack Publishing Company, Easton, Pa. (1985), and the 18th and 19th editions thereof, which are incorporated herein by reference.

The anti-IL-34 antibody in the composition preferably is formulated in an effective amount. An "effective amount" refers to an amount effective, at dosages and for periods of time necessary, to achieve the desired result, such as prevention or treatment of amyloid plaque formation. A "therapeutically effective amount" means an amount sufficient to influence the therapeutic course of a particular disease state. A therapeutically effective amount is also one in which any toxic or detrimental effects of the agent are outweighed by the therapeutically beneficial effects.

For therapeutic applications, the anti-IL-34 antibody of the invention is administered to a mammal, preferably a human, in a pharmaceutically acceptable dosage form such as those discussed above, including those that may be administered to a human intravenously as a bolus or by continuous infusion over a period of time, by intramuscular, intraperitoneal, intracerebrospinal, subcutaneous, intraarticular, intrasynovial, intrathecal, oral, topical, or inhalation routes.

Dosage regimens may be adjusted to provide the optimum response. For example, a single bolus may be administered, several divided doses may be administered over time, or the dose may be proportionally reduced or increased. The compositions of the invention can be administered to a subject to effect cell growth activity in a subject. As used herein, the term "subject" is intended to include living organisms in which apoptosis can be induced, and specifically includes mammals, such as rabbits, dogs, cats, mice, rats, monkey transgenic species thereof, and preferably humans.

It is understood that the administration routes, dosing schedules and optimal galenic forms can be determined according to the criteria generally taken into account when establishing a treatment suited to a patient such as, for example, the patient's age or body weight, the seriousness of his general state, his tolerance for the treatment and the side effects experienced.

The antibodies of the invention are particularly useful for treating IL-34-related disorder. As used herein, "IL-34-related disorders" refers to conditions or diseases resulting from the undesired activation of the IL-34 signaling pathway. Such conditions include e.g., inflammatory diseases, cancer, bone disease, skin diseases, metabolic diseases, cerebral diseases and hepatic diseases, amongst others.

According to another aspect, the invention relates to the anti-Il-34 antibody of the invention, or antigen-binding fragments thereof, as a medicament.

The invention also relates to the pharmaceutical composition of the invention as a medicament.

In another embodiment, the present invention also relates to the use of an antibody or of a pharmaceutical composition according to the invention for the preparation of a drug and/or a medicament for the prevention or the treatment of diseases mediated by IL-34 and/or involving IL-34 induced signalisation.

According to a particular aspect, the antibody, or an antigen-biding fragment thereof of the invention or the pharmaceutical composition are for use in the prevention and/or in the treatment of diseases selected from the list consisting of inflammatory diseases, cancer, bone disease, skin diseases, metabolic diseases, cerebral diseases and hepatic diseases and auto-immune diseases.

In particular, the anti-IL-34 antibodies of the invention may be used for the prevention or treatment of any disorder involving inflammation, either acute or chronic. Moreover, because of the relationship between the gut and the immune system as a whole, the objects of the invention may be used for the prevention or treatment of either local inflammation (i.e., inflammation of a specific tissue or a group of tissue) or systemic inflammation.

Since chronic systemic inflammation has been correlated to several non-immune diseases such as metabolic diseases, the objects of the invention are also useful in the prevention or treatment of diseases usually considered as "non-immune". The antibodies of the invention can be used to treat chronic systemic inflammation, also called low-grade systemic inflammation in order to prevent such diseases. The expression "low-grade chronic inflammation" should be understood in its general meaning in the field, i.e., it refers to a state characterized by a two-to threefold increase in the systemic concentrations of cytokines such as TNF-α, IL-6, and CRP, compared to healthy control.

As used herein, "inflammatory disease" preferably refers to acute pancreatitis; ALS; Alzheimer's disease; cachexia/anorexia; asthma; atherosclerosis; chronic fatigue syndrome, fever; diabetes (e.g., insulin diabetes); glomerulonephritis; graft versus host rejection; hemorrhagic shock; hyperalgesia, inflammatory bowel diseases; inflammatory conditions of a joint, including osteoarthritis, psoriatic arthritis and rheumatoid arthritis; ischemic injury, including cerebral ischemia (e.g., brain injury as a result of trauma, epilepsy, hemorrhage or stroke, each of which may lead to neurodegeneration); lung diseases (e.g., ARDS); multiple myeloma; multiple sclerosis; myelogenous (e.g., AML and CML) and other leukemias; myopathies (e.g., muscle protein metabolism, esp. in sepsis); osteoporosis; Parkinson's disease; pain; pre-term labor; psoriasis; reperfusion injury; septic shock; side effects from radiation therapy, temporal mandibular joint disease, tumor metastasis; or an inflammatory condition resulting from strain, sprain, cartilage damage, trauma, orthopedic surgery, infection or other disease processes.

In a particular embodiment of the invention, said inflammatory disease is chosen from inflammatory bowel diseases. According to the invention, inflammatory bowel diseases comprise Crohn's disease, ulcerative colitis, diverticulitis, and infectious colitis.

In a particular embodiment of the invention, said inflammatory disease is chosen from rheumatoid arthritis, osteoarthritis, and other inflammatory conditions resulting from strain, sprain, trauma, infection, cartilage damage or orthopedic surgery.

In a particular embodiment of the invention, said inflammatory disease is chosen from inflammatory joint disease, multiple sclerosis, leukemia, ischemic injury, or reperfusion injury.

The antibody of the invention can also be used to treat medical conditions which have an inflammatory component, such as for instance nephritis, skin diseases such as psoriasis, eczema, allergic dermatitis and hypersensitivity reactions and diseases of the central nervous system such as Alzheimer's disease, meningitis, multiple sclerosis and AIDS dementia.

The objects of the invention may further be used in the treatment or prevention of non-immune diseases with etiological origins in inflammatory processes, such as cancer, atherosclerosis, and ischemic heart disease.

According to a preferred embodiment, the anti-IL-34 antibody, or antigen-biding fragment thereof can be used for the treatment or prevention of diseases selected from the list consisting of inflammatory diseases wherein the inflammatory diseases are selected from the list consisting of rheumatoid polyarthritis, periodontitis, osteoporosis, periprosthetic osteolysis, Gougerot-Sjögren syndrome, atherosclerosis, arthritis, inflammatory and autoimmune skin pathologies, inflammatory bowel diseases (such as Crohn's disease, ulcerative colitis, diverticulitis, and infectious colitis), Alzheimer and neurodegenerative disorders, hepatic fibrosis such as e.g., non-alcoholic steatohepatitis (NASH), alcoholic steatohepatitis, viral-induced hepatic fibrosis, drug-induced steatohepatis and interstitial pulmonary fibrosis, such as e.g., inhaled substance associated fibrosis, drug induced fibrosis, autoimmune fibrosis, infectious fibrosis and idiopathic pulmonary fibrosis.

As used herein, the terms "cancer" and "cancerous" refer to or describe the physiological condition in mammals that is typically characterized by unregulated cell growth. The terms "cancer" and "cancerous" as used herein are meant to encompass all stages of the disease. Thus, a "cancer" as used herein may include both benign and malignant tumors.

In one embodiment of the invention, the cancer being treated is osteolysis, bone sarcomas (osteosarcoma, Ewing's sarcoma, Giant cell tumours of bone), bone metastases, glioblastoma and brain cancers, lung cancer, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

According to a preferred embodiment, the anti-IL-34 antibody of the invention is useful for treating diseases selected from the list consisting of tumour osteolysis; bone sarcomas (osteosarcoma, Ewing's sarcoma, Giant cell tumours of bone), bone metastases, glioblastoma and brain cancers, and lung cancer.

The effectiveness of the anti-IL-34 antibody of the invention in preventing or treating disease may be improved by administering said antibody serially or in combination with another agent that is effective for those purposes, such as tumor necrosis factor (TNF), an antagonist capable of inhibiting or neutralizing the angiogenic activity of acidic or basic fibroblast growth factor (FGF), platelet-derived growth factor (PDGF), or hepatocyte growth factor (HGF), an antagonist capable of inhibiting or neutralizing the coagulant activities of tissue factor, protein C, or protein S (see WO 91/01753), an antagonist such as an antibody capable of binding to HER2 receptor (see U.S. Pat. No. 5,772,997), or one or more conventional therapeutic agents such as, for example, alkylating agents, folic acid antagonists, antimetabolites of nucleic acid metabolism, antibiotics, pyrimidine analogs, 5-fluorouracil, cisplatin, purine nucleosides, amines, amino acids, triazol nucleosides, or corticosteroids.

In another aspect of the invention, the administration is combined with an administration of therapeutically effective amount of chemotherapeutic agent, such as for example, taxol (paclitaxel) or taxotere (docetaxel).

Chemotherapeutic agents include without any limitations, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and antifolate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors. In addition, the methods of the invention can be combined with another anti-cancer treatment, anti-angiogenic agent, or chemotherapeutic agent or radiation therapy. A preferred example is docetaxel or taxotere. Other examples include, gemcitabine, cisplatin diterpenoids and vinca alkaloids, paclitaxel, vinblastine, vincristine, and vinorelbine, carboplatin, cyclophosphamide, melphalan, and chlorambucil, busulfan, carmustine, dacarbazine, cyclophosphamide, melphalan, chlorambucil, busulfan, carmustine, dacarbazine, anti-neoplastic agents including, but not limited to, actinomycins such as dactinomycin, anthrocyclins such as daunorubicin and doxorubicin, bleomycins, epipodophyllotoxins, etoposide and teniposide; antimetabolite neoplastic agents, 5-fluorouracil, methotrexate, cytarabine, mecaptopurine, thioguanine, cannptothecins, irinotecan HCl, and topotecan HCl.

A variety of different chemotherapeutic agents or anti-cancer polypeptides can also be selected. Information sources such as www.clinicaltrials.gov, www.ncbi.nlm.nih, and www.drugs.com, include references to polypeptides and agents that can be selected.

Such other agents, e.g. anti-angiogenic agents or chemo-therapeutic agents may be present in the composition being administered or may be administered separately. In one aspect of the invention, the administration is performed with the other active principle, either simultaneously, separately or sequentially over time. When the administration is performed simultaneously, the two active principles may be combined in a single pharmaceutical composition, comprising the two compositions, such as a tablet or a gel capsule. On the other hand, the two active principles may, whether or not they are administered simultaneously, be present in separate pharmaceutical compositions. To this end, the combination may be in the form of a kit comprising, on the one hand, the anti-IL-34 antibody as described above and, on the other hand, the second active principle, the anti-IL-34 antibody as described above and the second active principle being in separate compartments and being intended to be administered simultaneously, separately, or sequentially over time.

The combination according to the present invention can be administered especially for tumor therapy in combination with chemotherapy, protein therapy (i.e. using a therapeutic agent such as an antibody or recombinant protein), gene therapy, radiotherapy, immunotherapy, surgical intervention, or a combination of these. Long-term therapy is equally possible as is adjuvant therapy in the context of other treatment strategies, as described above.

The antibodies or antibody fragments of the invention can also be used to detect IL-34 in a biological sample in vitro or in vivo.

A "biological sample" may be any sample that may be taken from a subject. Such a sample must allow for the determination of the presence of 11-34. The nature of the sample will thus be dependent upon the nature of the disorder. Preferred biological samples for the presence of 11-34 include samples such as a blood sample, a plasma sample, or a lymph sample, if the cancer is a liquid tumor. By "liquid tumor", it is herein referred to tumors of the blood or bone marrow, i.e. hematologic malignancies such as leukemia and multiple myeloma. Preferably, the biological sample is a blood sample.

A "biological sample" as used herein also includes a solid cancer sample of the patient to be tested, when the disorder is a solid cancer. Such solid cancer sample allows the skilled person to perform any type of measurement of the level of the biomarker of the invention. In some cases, the methods according to the invention may further comprise a preliminary step of taking a solid cancer sample from the patient. By a "solid cancer sample", it is referred to a tumor tissue sample. Even in a cancerous patient, the tissue which is the site of the tumor still comprises non tumor healthy tissue. The "cancer sample" should thus be limited to tumor tissue taken from the patient. Said "cancer sample" may be a biopsy sample or a sample taken from a surgical resection therapy.

In one embodiment, the anti-IL-34 antibodies of the invention are used to determine the level of IL-34 in a tissue or in cells derived from the tissue. In a preferred embodiment, the tissue is a diseased tissue. In a preferred embodiment of the method, the tissue is a tumor or a biopsy thereof. In a preferred embodiment of the method, a tissue or a biopsy thereof is first excised from a patient, and the levels of IL-34 in the tissue or biopsy can then be determined in an immunoassay with the antibodies or antibody fragments of the invention. In another preferred embodiment, the level of IL-34 is determined on a sample of a tissue or biopsy thereof, which can be frozen or fixed. The same method can be used to determine other properties of the IL-34 protein, such as its cell surface levels, or its cellular localization.

In one aspect the present invention comprises a method of detecting in vitro the presence and/or the location of IL-34 in a subject, said method comprising the steps of:
 a) contacting a sample of said subject with an antibody or antigen-binding fragments thereof as described above; and
 b) detecting the binding of said antibody with the sample.

The ability to use the anti-IL-34 antibodies to detect 11-34 in a biological sample in vitro or in vivo is advantageous for diagnosing the presence of an IL-34-related disorder in a patient. The above-described method can be used to diagnose an IL-34-related disorder in a patient, wherein the level of IL-34 measured in said patient is compared with that of a normal reference subject or standard. In particular, said method can be used to determine whether a tumor expresses 11-34, which may suggest that the tumor will respond well to treatment with the antibodies, antibody fragments or antibody conjugates of the present invention.

As used herein, "diagnosis" or "identifying a subject having" refers to a process of determining if an individual is afflicted with a disease or ailment (e.g., an IL-34-related disorder). An IL-34-related disorder is diagnosed for example by detecting the 11-34 in a biological sample of a patient in vitro or in vivo.

In another aspect the present invention relates to a method of diagnosing any one of diseases as cited in the list consisting of inflammatory diseases, cancer, bone disease, skin diseases, metabolic diseases, cerebral diseases and hepatic diseases and auto-immune diseases in a subject known to or suspected to have a such disease, said method comprising:
 a) contacting cells of said patient with an antibody or one of its antigen-binding fragment according to the invention,
 b) measuring the binding of said antibody or its of its antigen binding fragment to said cells, and
 c) comparing the expression in part (b) with that of a normal reference subject or standard.

The present invention further provides for monoclonal antibodies, chimeric antibodies, humanized antibodies and epitope-binding fragments thereof that are further labeled for use in research or diagnostic applications. In a preferred embodiment, the invention relates to a kit comprising at least the antibody, or an antigen-biding fragment thereof of the invention, said antibody or antigen-biding fragment thereof being preferably labeled.

In a further preferred embodiment, the label is a radiolabel, a fluorophore, a chromophore, an imaging agent or a metal ion.

A method for diagnosis is also provided in which said labeled antibodies or epitope-binding fragments thereof are administered to a subject suspected of having a cancer or an inflammatory disease or an autoimmune disease, and the distribution of the label within the body of the subject is measured or monitored.

The examples that follow are merely exemplary of the scope of this invention and content of this disclosure. One skilled in the art can devise and construct numerous modifications to the examples listed below without departing from the scope of this invention.

FIGURE LEGENDS

Figure 2:
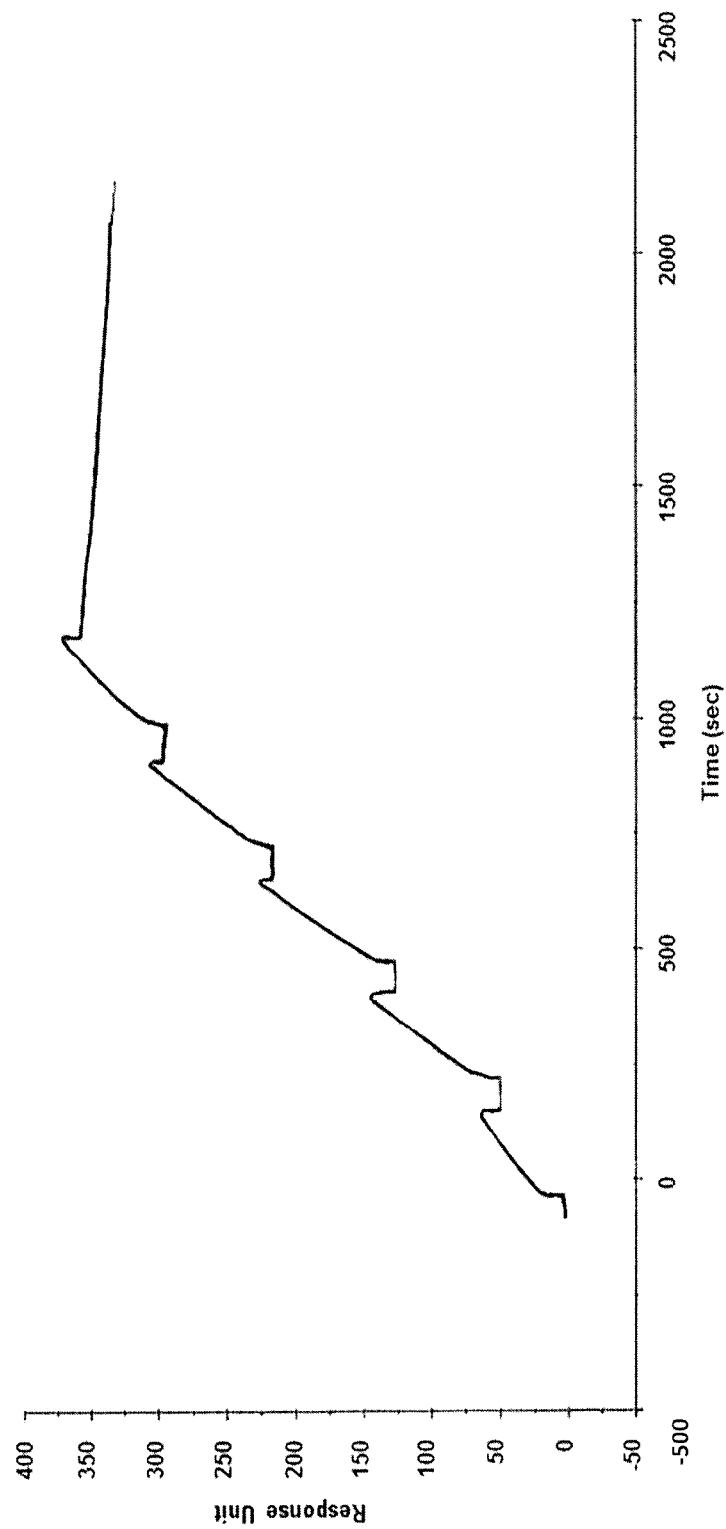
Figure 3:
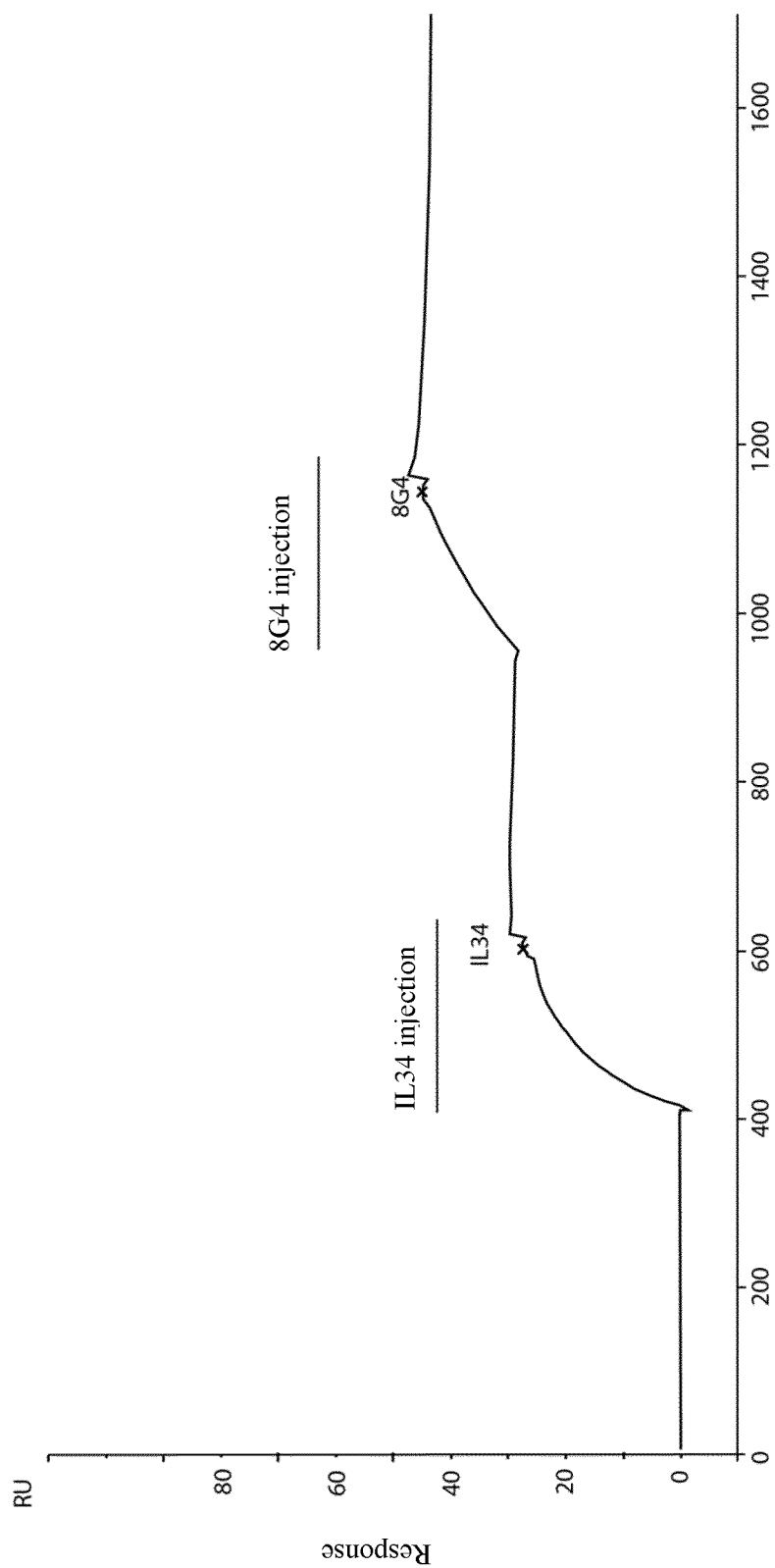
Figure 4:
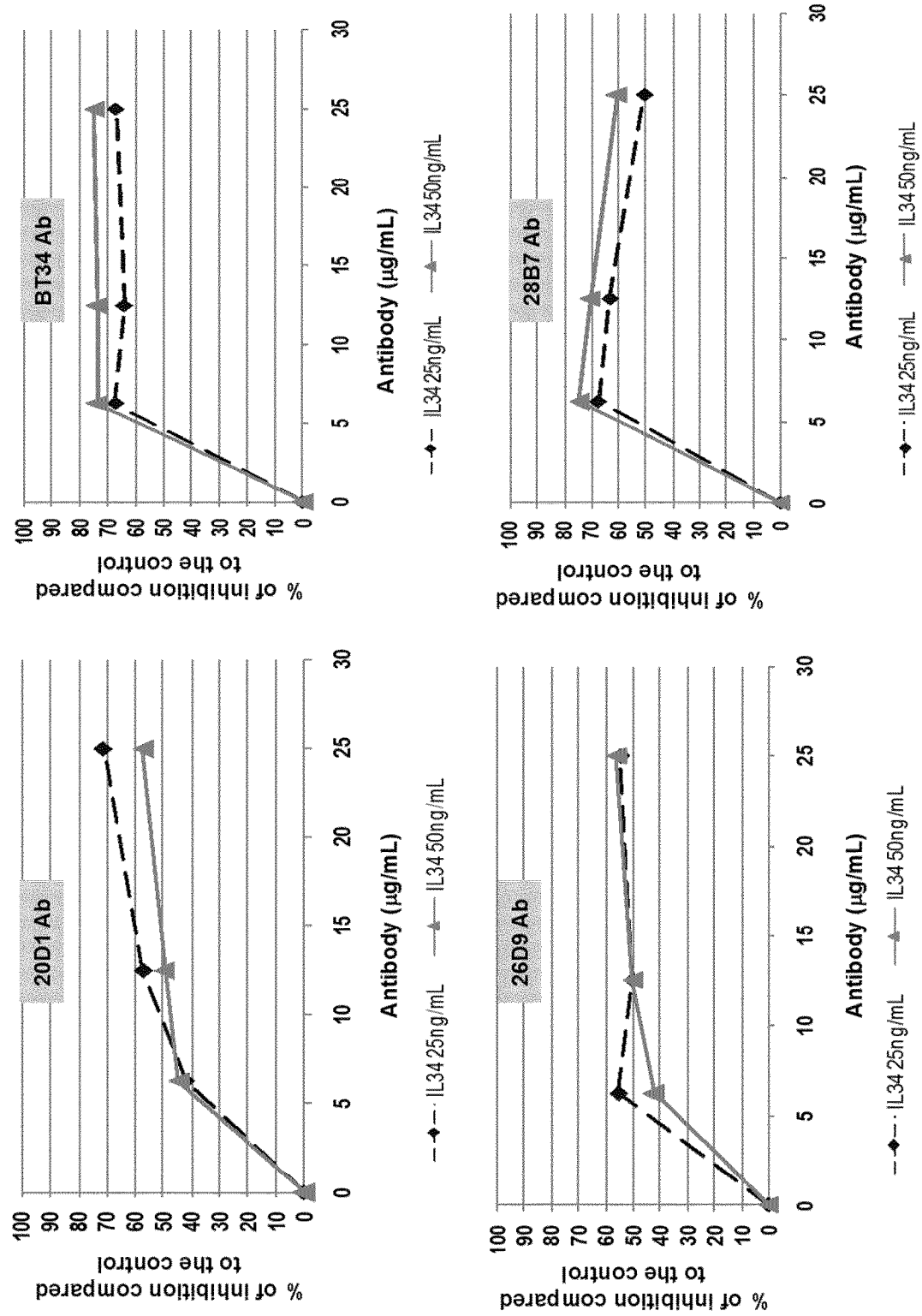
Figure 5:
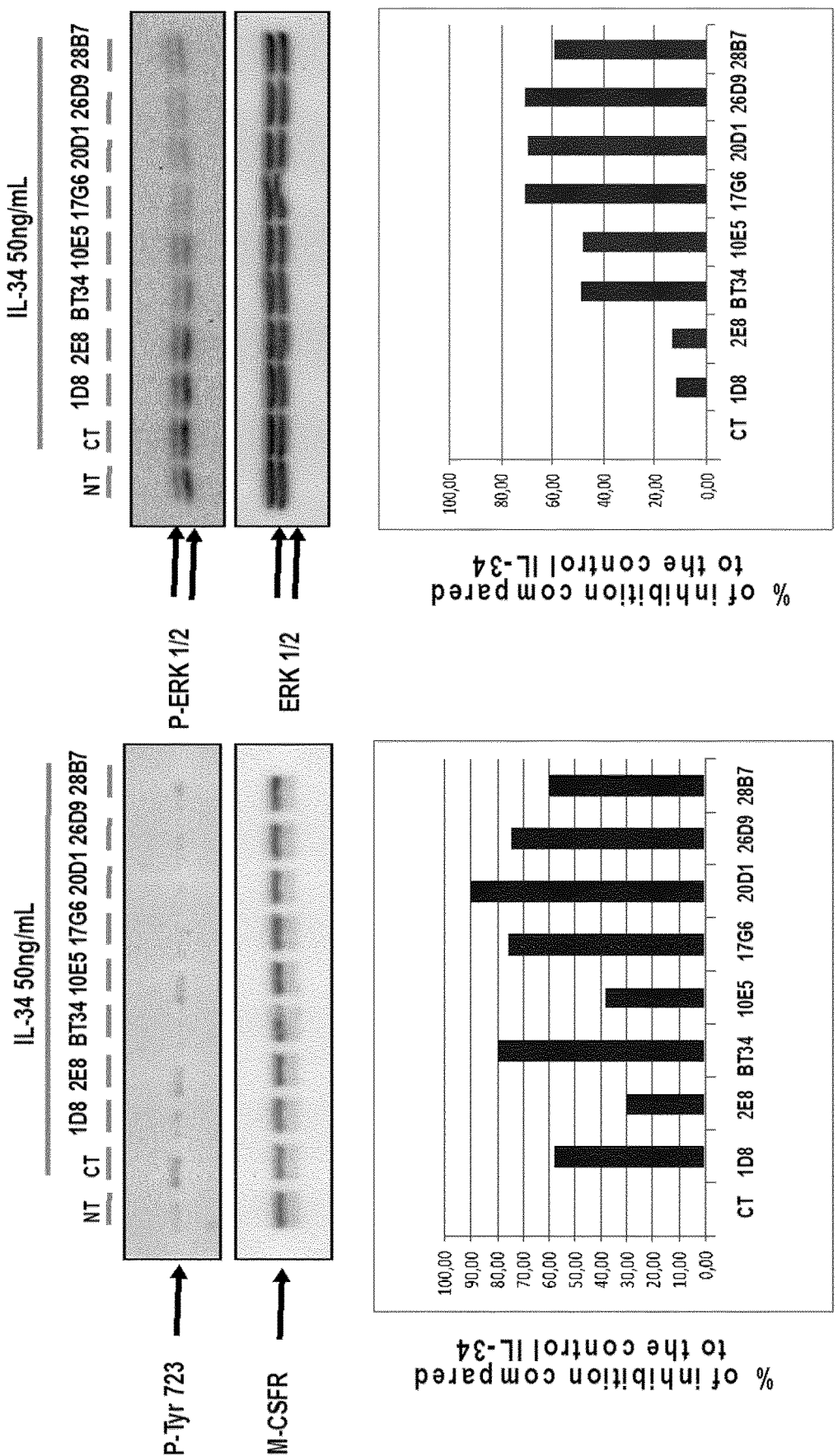
Figure 6A:
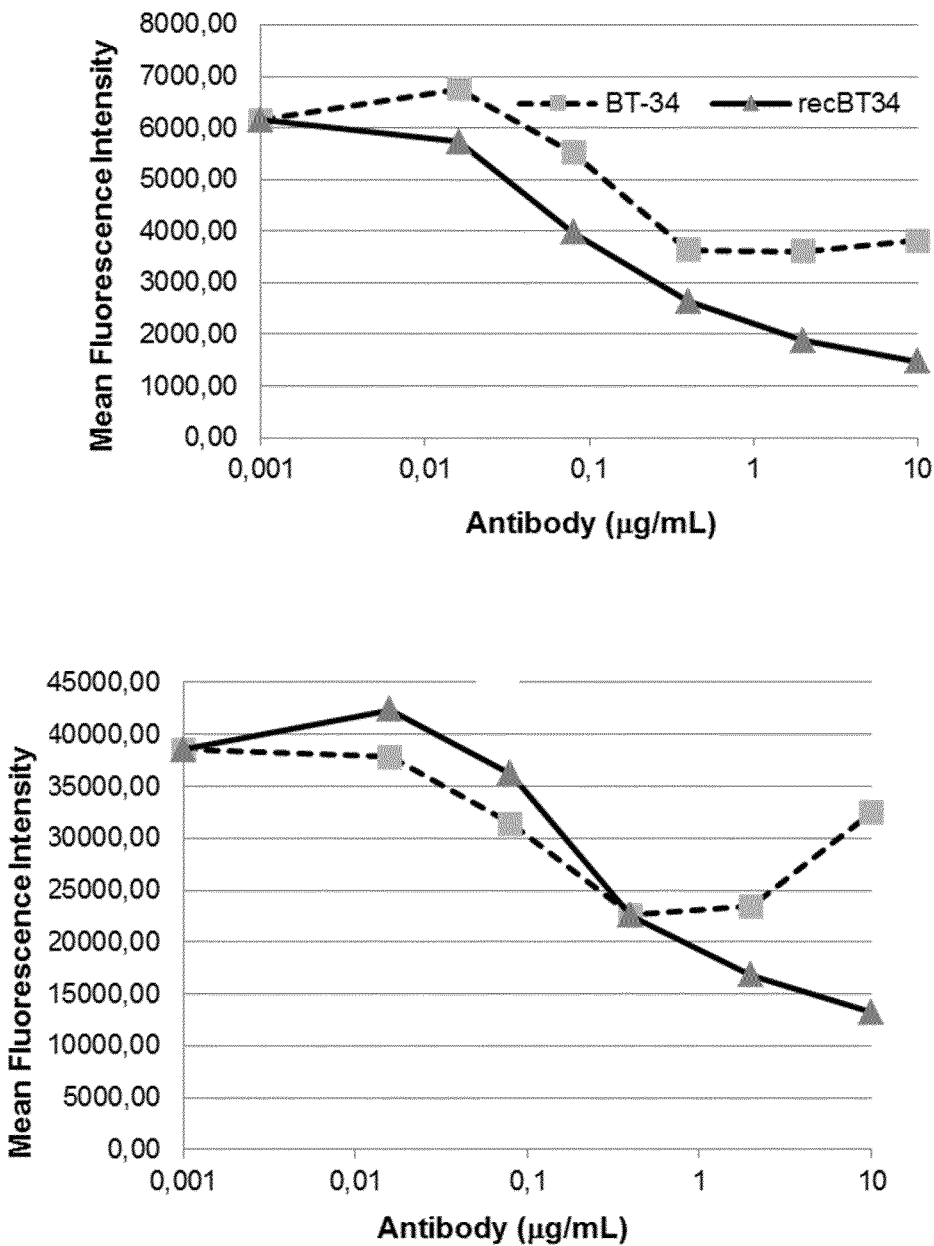
Figure 6B:
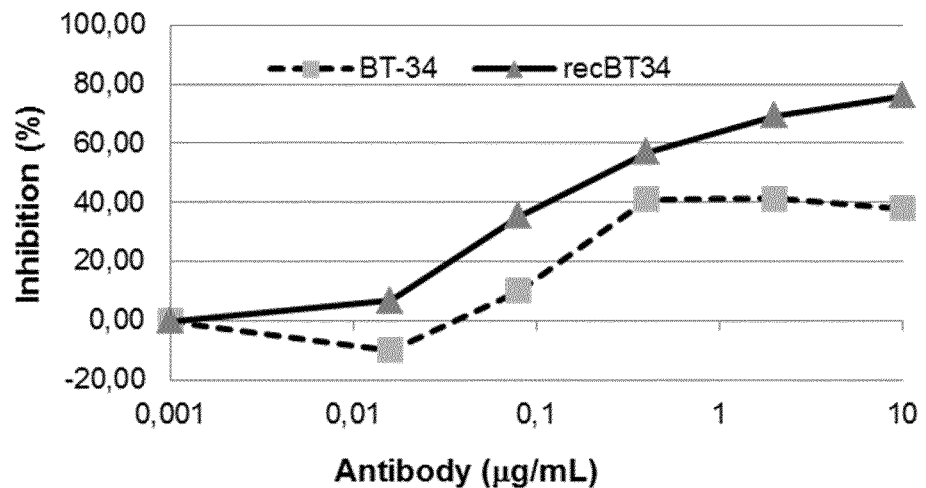
Figure 6B:
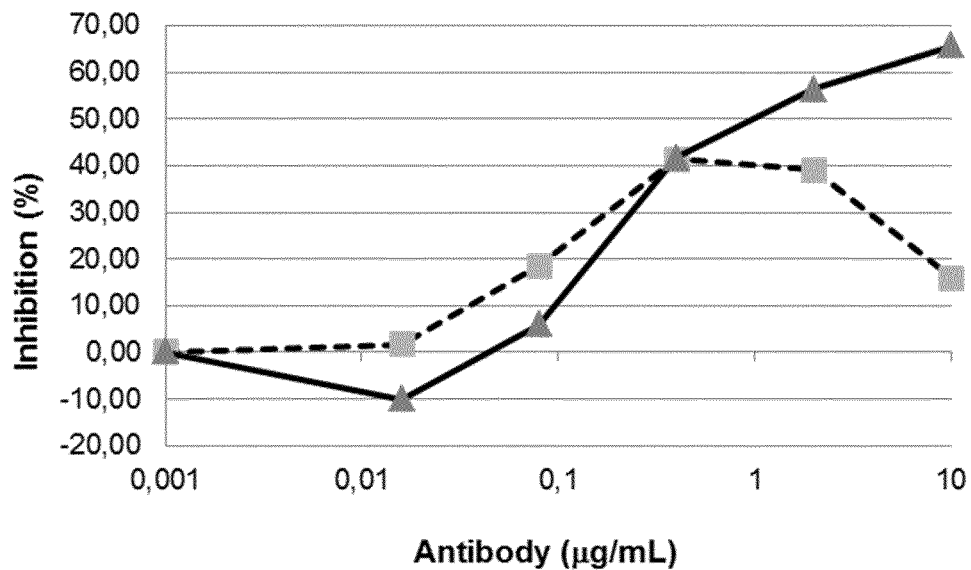
Figure 7A:
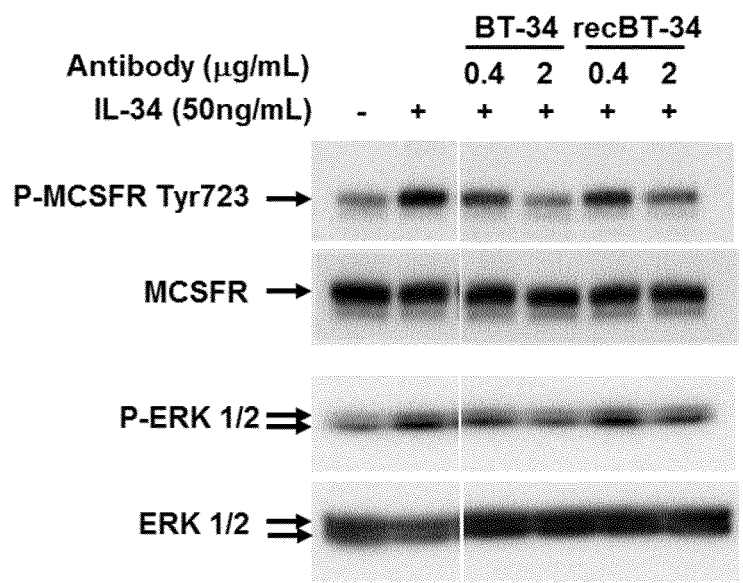
Figure 7A:
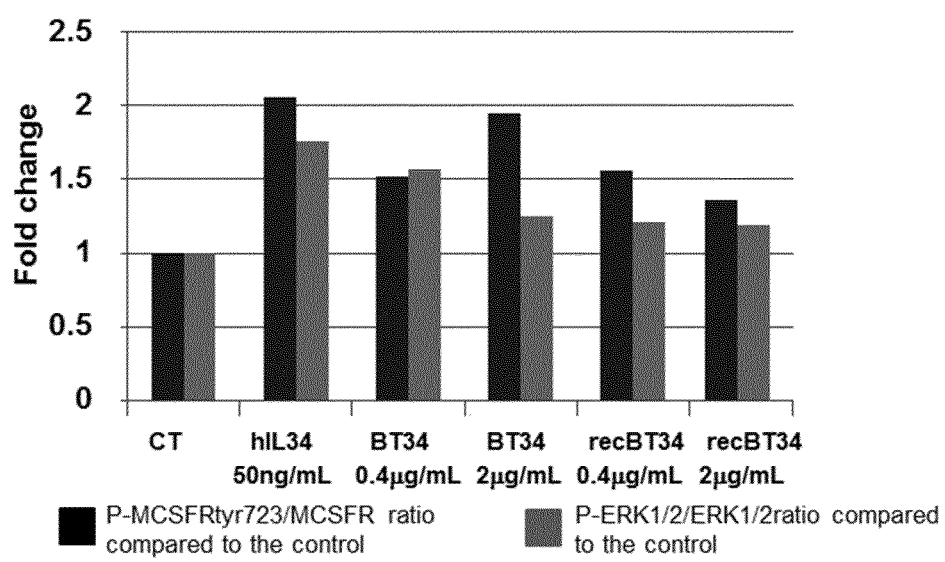
Figure 7B:
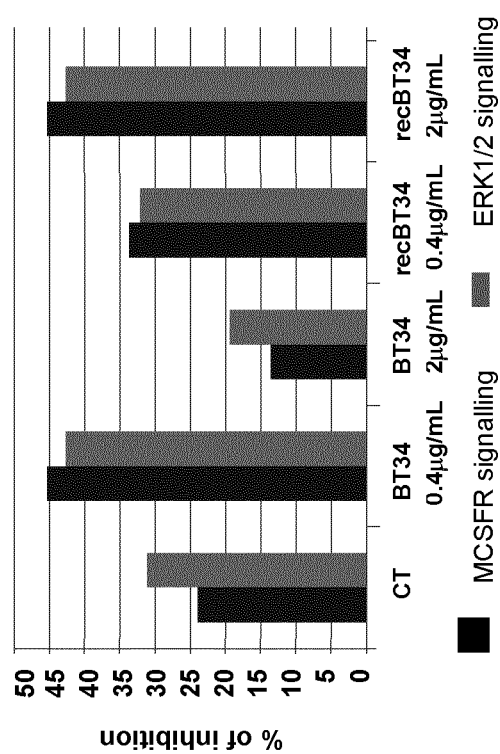

FIG. 1: Analysis by Agilent instrument of anti-IL-34 mRNA integrity after RNA extraction;

FIG. 2: Sensogram after correction of the reference obtained from SPR interaction curves for various concentration of IL-34, showing the interaction of IL-34 with anti-IL-34 antibody;

FIG. 3: Sensogram after correction of the reference obtained from SPR interaction curves for 50 nM of IL-34 and 10 nM of anti-IL-34;

FIG. 4: Inhibition of proliferation/survival of isolated human CD14$^+$ monocytes by anti-IL-34 antibodies;

FIG. 5: Inhibition of IL34-induced cell signalization by anti-IL-34 antibodies;

FIG. 6: (A) Human CD14+ viability measured by fluorescence Intensity and (B) Inhibition of proliferation/survival of isolated human CD14$^+$ monocytes by murine anti-IL-34 antibodies (BT34) compared to recombinant IL-34 antibodies (chimeric antibodies clone rec-BT34);

FIG. 7: (A) Western blot and western blot quantification and (B) Inhibition of IL34-induced cell signalization by murine anti-IL34 antibodies (clone BT34) compared to recombinant IL-34 antibodies (chimeric antibodies clone recBT34).

EXAMPLES

1. Sequencing Data—Murine IL-34 Antibodies
Summary of the Process
a) Cellular culture
b) Total RNA extraction
c) Reverse transcription of the RNA (primer oligodT)
d) Amplification of variable chains by PCR (various primer pairs)
e) Cloning of the amplicons in shuttle vector
f) Sequencing of the inserts
g) Sequence analysis
RNA Extraction The full analysis and results for mRNA extraction are shown in table 2 below.

TABLE 2

| Clone | Cell nb × $10^6$ | Volume (µl) | conc ng/µl | RNA yield [µg] | RNA purity $A_{260}/A_{280}^2$ |
|---|---|---|---|---|---|
| Anti-IL-34 BT34 clone | 25 | 250 | 1020 | 255 | 2.08 |

The analysis of mRNA integrity is done using the Agilent instrument (cf. FIG. 1).

Monoclonal Antibodies Sequencing from B-T34

Sequencing data were analyzed on the IgBlast database. The sequences corresponding to complete variables chains of antibody are presented in the annexed sequence listing.

The analysis of the sequencing data shows that this sequences coding light and heavy chain variable domain is complete and functional.

2. Chimerization of the Antibodies Anti-IL-34 of the Invention

The chimeric antibodies anti-IL-34 of the invention are obtained by following protocol:

The DNA sequences encoding the variable domains of the tight and heavy chains are introduced by ligature restriction in two type P115 expression vectors respectively encoding the human constant domains of the heavy chain (IgG1 isotype) and the light chain (isotype Kappa), forming a heavy chain PTT5 vector and a light chain PTT5 vector. After controlling the obtained sequence, these two vectors are amplified in order to perform their transfection into HEK-EBNA cells cultivated in serum free stirred mode conditions. The transfection is carried out by using a lipofection agent (JET PEI) and the cells are then cultivated for a week with slow stirring. The secretion of recombinant antibodies (chimeric antibodies) is then monitored using an ELISA assay (Kit FASTELISA RD-Biotech) every two days after the transfection. The cell culture is stopped after 7 days and the supernatant is collected by centrifugation. Chimeric recombinant antibodies are then purified from the supernatant by affinity chromatography on protein A (Repligen corp.). The purified antibodies are tested by SDS-PAGE electrophoresis and their specificity is firstly controlled by ELISA and then, by the bioassay which allows controlling the original murine antibody properties.

3. Humanization of the Antibodies Anti-IL-34

During the humanization step, the murine sequences present in the chimeric antibody are analyzed for each amino acid and compared with databanks in order to mimic a human sequence. The construction of 5 to 10 humanization variants is performed by DNA neosynthesis. After synthesis of DNA encoding these variants (humanized heavy chain and humanized light chain) the sequences are subcloned by ligature restriction into PTT5 vectors described above. The vectors encoding the different variants are then transfected using the same conditions and in the same cells as previously described in order to obtain the different humanized antibody variants which are purified as described above. The characterization of these variants and the analysis of their performance are performed as for the chimeric antibodies.

For clinical purpose, the humanized antibodies may be produced in CHO cells.

4. Analysis of Interaction Between Antibody Anti-IL-34 of the Invention and Recombinant Protein IL-34 and Measuring of Kd, Kon and Koff.

4.1. Methods and Materials

BIACore™ T 100 system has been used in order to analyze the interaction between anti-IL-34 and the recombinant IL-34.

The following microarrays: CM5 (CM-dextran, 1-ethyl-3-(3-diaminopropyl) carbodiimide hydrochloride (EDC) and N-Hydroxysuccinimide (NHS) have been purchased by GE Healthcare BIAcore and used according to manufacture instructions.

A polyclonal ant-mouse antibody was immobilized covalently on the CM5 microarray surface, thus allowing capturing IL-34 antibody as ligand. Capture level of anti-IL-34 is comprised between 700 and 1000 RU (resonance unity).

A control channel anti-IL-34 was prepared as indicated above without in order to assess nonspecific interaction on the microarray's surface.

Theses interaction were performed at 25° C., in HBS-P+ buffer (HEPES 10 mM pH 7.4; NaCl 150 mM; P20 0.05%) by administrating different concentrations of IL-34 obtained by serial dilution of the protein IL-34 (Peprotech Ref 200-34, whole protein without signal peptide with His tag on C-terminal).

The interaction kinetics are performed without regeneration between each administration.

The regeneration is performed by administering 10 mM of Glycine-HCl buffer at pH=1.7 allowing dissociating the antibody IL-34 from immobilized polyclonal antibody.

4.2. Results

The obtained results are shown by sensograms of FIG. 2. The sensograms have been analyzed via 1:1 mathematic pattern allowing adjusting the obtained values shown in table 3 below.

TABLE 3

| $k_a$ (M$^{-1}$S$^{-1}$) | $k_d$ (s$^{-1}$) | $K_D$ (M) |
|---|---|---|
| $3.1 \pm 0.4 \times 10^{+4}$ | $2.9 \pm 2.3 \times 10^{-7}$ | $9.4 \pm 7 \times 10^{-12}$ |

Obtained sensograms show a slow association between IL-34 and the anti-IL-34 antibody BT34 (Ka is about $3 \times 10^4 M^{-1}S^{-1}$) and a very low dissociation (Kd<10-6s-1).

Thus, these resultants clearly demonstrate that interaction between IL-34 and the anti-IL-34 antibody is very stable and consequently, that the binding activity is very high.

Furthermore, obtained dissociation during the IL-34 and the anti-IL-34 antibody interaction was so weak that it was impossible to determine it by presently used tools.

5. Immobilization of the Receptor 5.1. Methods and Materials

The measurement of surface plasmon resonance (SPR) was performed on BIACore T100. The microarrays CM5 (CM-dextran, 1-ethyl-3-(3-diaminopropyl) carbodiimide hydrochloride (EDC) and N-Hydroxysuccinimide (NHS) have been purchased by GE Healthcare BIAcore and used according to manufacture instructions.

The ligand, M-CSF receptor (R&D-Systems ref: 329-MR) was immobilized covalently on the CM5 microarray surface. Capture level of anti-IL-34 is comprised between 600 and 800 RU.

A control channel without protein was prepared as indicated previously in order to assess nonspecific interaction on the microarray's surface.

Theses interaction were performed at 25° C., in HBS-P+ buffer (HEPES 10 mM pH 7.4; NaCl 150 mM; P20 0.05%). The microarray was regenerated before each interaction.

5.2. Results

Positive Control: Interaction IL-34/M-CSF-R

Different concentrations (10 nM, 20 nM and 50 nM) of IL-34 protein were administered on the microarray surface comprising the immobilized receptor M-CSF-R.

An interaction signal of about 20 RU was observed with only 50 nM of IL-34.

During previously performed assays-receptor capture on the microarray surface) for lower level of immobilization (about 100-200 RU), the interaction signal was observed after administration of 20 nM IL-34.

The above results show that there are several type of receptors immobilized on the microarray surface.

As previously mentioned, the regeneration of microarray was difficult because receptors immobilization on the microarray surface was weak.

Thus, it was difficult to assess IL-34/anti-IL-34 antibody with increasing concentrations of the antibody.

For this purpose, in order to perform the assays without errors, novel microarrays were performed as indicated above, for each assessed concentration of the anti-IL-34 antibody BT34.

Negative Control 10 nM of the anti-IL-34 antibody were injected on the microarray surface. No signal was observed showing that there is no interaction between the anti-IL-34 antibody and the M-CSF-R receptor.

Inhibiting Assay

The inhibiting assay was performed in order to measure signal emitted during the interaction between IL-34 and M-CSF-R.

IL-34 protein was incubated with large quantity of the anti-IL-34 antibody BT34 (50 nM/1 µM). In these experimental conditions no signal was observed. This indicates that in presence of high concentrations of the anti-IL-34 antibody, IL-34 protein does not interact with its receptor.

After that, 50 nM of IL-34 protein was injected on the microarray surface.

As shown on FIG. 3 the obtained sensogram (about 30 RU) demonstrates that the interaction between IL-34 and its receptor is stable.

After that 10 nM of anti-IL-34 antibody were injected and a signal demonstrating the interaction of IL-34 with the anti-IL-34 antibody was observed (FIG. 3).

These assays demonstrate that IL-34 interact with its receptor M-CSF-R on the microarray surface. Even though the antibody is capable of interacting with IL-34 when bound to its receptor, the interaction between IL-34 and its receptor is inhibited when the antibody anti-IL-34 is incubated with IL-34 before the interaction of this protein with its receptor.

Thus, these data demonstrate that the anti-IL-34 antibody epitope is distinct of the interaction site between IL-34 and its receptor and that the inhibitory effect is due to steric configuration of complex protein/antibody.

Consequently, it is demonstrated that the antibodies of the invention are capable of binding the cytokine IL-34 even when this one is binded to its receptor which allow increasing the therapeutical efficiency of these antibodies.

6. Inhibitory Effect of Murine Anti-IL-34 Antibodies on Cell Proliferation 6.1. Materials and Methods Isolation of Human CD14$^+$ Monocytes and Analysis of Cell Proliferation Human CD14$^+$ monocytes were initially isolated from human peripheral blood donors provided by the French blood bank institute (Etablissement Français du Sang, Nantes, France, authorization number: NTS 2000-24), by using MACS microbeads (MiltenyiBiotec, Germany). Cells were cultured in the presence of 25 ng/mL or 50 ng/mL of IL-34, with or without increased concentrations of anti-IL-34 antibodies. The effects of treatments on CD14$^+$ survival/proliferation were determined by measuring metabolic activity using an Alamar Blue® assay. Forty thousand cells per well were put into 96-well plates with α-MEM and the corresponding treatments. After 3 days, Alamar Blue® reagent was added and the fluorescence produced was read in the linear range (excitation 530 nm/emission 600 nm).

6.2. Results

In order to test whether the antibody murine anti IL-34 (clone BT34) is capable of inhibiting IL-34 dependent cell proliferation, increasing amounts of the antibody were added to IL-34 stimulated monocytes. As shown in FIG. 4, this antibody at a concentration of ca. 5 lag/mL was capable of preventing the proliferation of about 70% of the CD14+ cells. The same level of inhibition was observed with higher concentrations of antibody. In contrast, other Il-34 antibodies (20D1 and 26D9) failed to yield such a potent effect. Finally, a third anti-IL-34 control antibody prevented the proliferation of about 70% of the monocytes at a low concentration (ca. 5 µg/mL). However, the percentage of inhibition decreased when higher concentrations of antibody were used, raising doubts about the utility of this antibody. On the other hand, BT34 led to the same level of inhibition, regardless of whether 5 or 25 µg/mL are used.

Thus, the BT34 anti-IL-34 antibody can be used successfully for preventing and/or treating proliferative diseases such as cancer.

7. Inhibitory Effect of Murine Anti-IL-34 Antibodies on Cell Signalization 7.1 Materials and Methods Western Blot Analysis The M-CSFR expressing cells treated or not with 50 ng/mL of human IL-34 with or without 2 mg/mL of anti-Il-34 antibodies (clones 1D8, 2E8, BT34, 10E5, 17G6, 20D1, 26D9, 2867) for 10 minutes, were collected in a RIPA buffer (10 mM Tris pH8, 1 mM EDTA, 150 mM NaCl, 1% NP40, 0.1% SDS containing a cocktail of protease and phosphatase inhibitors: 1 mM sodium orthovanadate ($Na_2VO_4$), 1 mM phenylmethylsulforyl fluoride (PMSF), 10 mM sodium fluoride (NaF), 10 mM N-ethylmaleimide (NEM), 2 µg/ml leupeptin and 1 µg/ml pepstatine). The protein concentration was determined using a BCA (bicinchoninic acid) protein assay (Sigma Aldrich). 40 µg of total protein extracts were prepared in a Laemmli buffer (62.5 mM Tris-HCl, pH 6.8, 2% SDS, 10% glycerol, 5% 2-mercaptoethanol, 0.001% bromophenol blue) and then separated by SDS-polyacrylamide gel electrophoresis. After electrophoretic transfer, the immobilon-P membranes (Millipore, Molsheim, France) were blotted with the primary antibodies. Primary antibodies directed against human P-MCSFR (Tyr-723), P-Erk1/2, and the total form of proteins were purchased from Cell Signalling (Ozyme, Saint Quentin Yvelines, France). The membranes were then probed with secondary antibodies coupled with horseradish peroxidase. Antibody binding was visualised with a Pierce enhanced chemiluminescence (ECL) kit (ThermoSientific, Illkirch, France). The luminescence detected with a Charge Couple Device (CCD) camera was quantified using the GeneTools programme (Syngene, Cambridge, United Kingdom).

7.2. Results

As shown on FIG. 5, IL-34-dependent Tyr-phosphorylation of the MCSF receptor is blocked by the BT34 antibodies. Likewise, activation of ERK 1/2 is prevented by this antibody. These results are consistent with the capacity of BT34 to inhibit the IL-34-mediated proliferation of cells.

8. Inhibitory Effect of Murine Anti-IL-34 Antibodies on Cell Proliferation Compared to the Inhibitory Effect of Recombinant Anti-IL-34 (Chimeric Antibody recBT34)

8.1. Materials and Methods

Isolation of Human $CD14^+$ Monocytes and Analysis of Cell Proliferation

Human $CD14^+$ monocytes were initially isolated from human peripheral blood donors provided by the French blood bank institute (Etablissement Français du Sang, Nantes, France, authorization number: NTS 2000-24), by using MACS microbeads (MiltenyiBiotec, Germany). Cells were cultured in the presence of IL-34, with recombinant anti-IL-34 antibody (chimeric antibody recBT34) and with murine anti-IL-34 antibody (clone BT34). The effects of treatments on $CD14^+$ survival/proliferation were determined by measuring metabolic activity using an Alamar Blue® assay. Forty thousand cells per well were put into 96-well plates with α-MEM and the corresponding treatments. After 3 days, Alamar Blue® reagent was added and the fluorescence produced was read in the linear range (excitation 530 nm/emission 600 nm).

8.2. Results

As shown on FIGS. 6 (A and B) the recombinant anti-IL-34 (rec-BT34) antibodies markedly inhibited human CD14+ cell viability and with more efficiency than the murine IL-34 antibodies (clone BT34).

Thus, the recombinant anti-IL-34 antibody can also be used successfully for preventing and/or treating proliferative diseases such as cancer.

9. Inhibitory Effect of Murine Anti-IL-34 Antibodies (Clone BT34) Compared to the Inhibitory Effect of the Recombinant IL-34 Antibody (Chimeric Antibody recBT34) on Cell Signalization 9.1. Materials and Methods Western Blot Analysis The M-CSFR expressing cells treated with 50 ng/mL of human IL-34 with 0.4 µg/ml or 2 g/ml of murine anti-Il-34 antibody (clone BT34) and with of 0.4 µg/ml or 2 g/ml recombinant anti IL-34 antibody (rec-BT34) for 10 minutes, were collected in a RIPA buffer (10 mM Tris pH8, 1 mM EDTA, 150 mM NaCl, 1% NP40, 0.1% SDS containing a cocktail of protease and phosphatase inhibitors: 1 mM sodium orthovanadate ($Na_2VO_4$), 1 mM phenylmethylsulforyl fluoride (PMSF), 10 mM sodium fluoride (NaF), 10 mM N-ethylmaleimide (NEM), 2 µg/ml leupeptin and 1 µg/ml pepstatine). The protein concentration was determined using a BCA (bicinchoninic acid) protein assay (Sigma Aldrich). 40 µg of total protein extracts were prepared in a Laemmli buffer (62.5 mM Tris-HCl, pH 6.8, 2% SDS, 10% glycerol, 5% 2-mercaptoethanol, 0.001% bromophenol blue) and then separated by SDS-polyacrylamide gel electrophoresis. After electrophoretic transfer, the immobilon-P membranes (Millipore, Molsheim, France) were blotted with the primary antibodies. Primary antibodies directed against human P-MCSFR (Tyr-723), P-Erk1/2, and the total form of proteins were purchased from Cell Signalling (Ozyme, Saint Quentin Yvelines, France). The membranes were then probed with secondary antibodies coupled with horseradish peroxidase. Antibody binding was visualised with a Pierce enhanced chemiluminescence (ECL) kit (ThermoSientific, Illkirch, France). The luminescence detected with a Charge Couple Device (CCD) camera was quantified using the GeneTools programme (Syngene, Cambridge, United Kingdom).

9.2. Results

As shown on FIGS. 7 (A and B), IL-34-dependent Tyr-phosphorylation of the MCSF receptor is blocked by all anti-IL-34 antibodies. Likewise, activation of ERK 1/2 is prevented by this antibody. These results are consistent with the capacity of anti-IL-34 antibodies to inhibit the IL-34-mediated proliferation of cells.

FIGS. 7 (A and B) also shows that the recombinant anti-IL-34 antibody (chimeric antibody recBT34) inhibits hIL-34 induced signalization in MCSFR overexpressing HEK293 in a similar manner compared to murine anti-IL-34 antibody BT34.

REFERENCES

Cronk J C, Kipnis J. Microglia—the brain's busy bees. F1000Prime Rep. (2013); 5:53.

Dai X. M., G. R. Ryan, A. J. Hapel, M. G. Dominguez, R. G. Russell, S. Kapp, V. Sylvestre, E. R. Stanley, Targeted disruption of the mouse colony-stimulating factor 1 receptor gene results in osteopetrosis, mononuclear phagocyte deficiency, increased primitive progenitor cell frequencies, and reproductive defects, Blood 99 (2002) 111-120.

Felix J., J. Elegheert, I. Gutsche, A. V. Shkumatov, Y. Wen, N. Bracke, E. Pannecoucke, I. Vandenberghe, B. Devreese, D. I. Svergun, E. Pauwels, B. Vergauwen, S. N. Savvides, Human IL-34 and CSF-1 establish structurally similar extracellular assemblies with their common hematopoietic receptor, Structure 21 (2013) 528-539.

Foucher E. D., S. Blanchard, L. Preisser, E. Garo, N. Ifrah, P. Guardiola, Y. Delneste, P. Jeannin, IL-34 Induces the Differentiation of Human Monocytes into Immunosuppressive Antagonistic Effects of GM-CSF and IFNγ, PloS One 8 (2013) e56045.

Lin H., E. Lee, K. Hestir, C. Leo, M. Huang, E. Bosch, R. Halenbeck, G. Wu, A. Zhou, D. Behrens, D. Hollenbaugh, T. Linnemann, M. Qin, J. Wong, K. Chu, S. K. Doberstein, L. T. Williams, Discovery of a Cytokine and Its Receptor by Functional Screening of the Extracellular Proteome, Science 320 (2008) 807-811.

Liu H., C. Leo, X. Chen, B. R. Wong, L. T. Williams, H. Lin, X. He, The mechanism of shared but distinct CSF-1R signaling by the non-homologous cytokines IL-34 and CSF-1, Biochim. Biophys. Acta 1824 (2012) 938-945.

Ma X., W. Y. Lin, Y. Chen, S. Stawicki, K. Mukhyala, Y. Wu, F. Martin, J. F. Bazan, Needterman S B, Wunsch C D. A general method applicable to the search for similarities in the amino acid sequence of two proteins. J Mol Blot. 48(1970):443-53.

Pearson W R, Lipman D J. Improved tools for biological sequence comparison. Proc Natl Acad Sci USA. 85(1988):2444-8.

Ries C H, Cannarite M A, Hoves S2, Benz J, Wartha K, Runza V, Rey-Giraud F, Pradel L P, Feuerhake F, Klaman I, Jones T, Jucknischke U, Scheibtich S, Katuza K, Gorr I H, Walz A, Abiraj K, Cassier P A, Sica A, Gomez-Roca C, de Visser K E, Italiano A, Le Tourneau C, Delord J P, Levitsky H, Bay J Y, Rüttinger D. Targeting tumor-associated macrophages with anti-CSF-1R antibody reveals a strategy for cancer therapy. Cancer Celt 25(2014):846-59.

Roth P., E. R. Stanley, The biology of CSF-1 and its receptor, Curr. Top. Microbiol. Immunol. 181 (1992) 141-167.

Ségaliny A I, Mohamadi A, Dizier B, Lokajczyk A, Brion R, Lanel R, Amiaud J, Charrier C, Boisson-Vidal C, Heymann D. Interleukin-34 promotes tumour progression and metastatic process in osteosarcoma through induction of angiogenesis and macrophage recruitment. Int J Cancer. 2014 in press.

Smith, T. F. and Waterman, M. S. Comparison of biosequences, Adv. Appl. Math., 2 (1981) 482-489.

Stanley E R, Chitu V. CSF-1 receptor signaling in myeloid cells. Cold Spring Harb Perspect Biol (2014) 2; 6.

Starovasnik M. A., Structural Basis for the Dual Recognition of Helical Cytokines IL-34 and CSF-1 by CSF-1R, Structure 20 (2012) 676-687.

Tatusova T A, Madden T L. BLAST 2 Sequences, a new tool for comparing protein and nucleotide sequences FEMS Microbiol Lett. 174 (1999) 247-50.

Verhoeyen M, Riechmann L. Engineering of antibodies. Bioessays. 8 (1988):74-8.

Wang Y, Colonna M. Interkeukin-34, a cytokine crucial for the differentiation and maintenance of tissue resident macrophages and Langerhans cells. Eur J Immunol (2014) 44:1575-81.

Wei S., S. Nandi, V. Chitu, Y. G. Yeung, W. Yu, M. Huang, L. T. Williams, H. Lin, E. R. Functional overlap but differential expression of CSF-1 and IL-34 in their CSF-1 receptor-mediated regulation of myeloid cells. J Leukoc Biol. 88 (2010) 495-505.

Ye J, Ma N, Madden T L, Ostell J M. IgBLAST: an immunoglobulin variable domain sequence analysis toot, Nucleic Acids Res. 41 (Web Server issue) (2013) W34-40.

WO 2013/119716.

---

The invention claimed is:

1. An anti-IL-34 antibody or an antigen-binding fragment thereof, said antibody comprising: a light chain comprising CDR-L1 of SEQ ID NO:1, CDR-L2 of SEQ ID NO:2, and CDR-L3 of SEQ ID NO:3; and a heavy chain comprising CDR-H1 of SEQ ID NO:4, CDR-H2 of SEQ ID NO:5, and CDR-H3 of SEQ ID NO:6.

2. The antibody or an antigen-binding fragment thereof of claim 1, said antibody comprising a light chain comprising SEQ ID NO:7 and a heavy chain comprising SEQ ID NO:8.

3. The antibody or an antigen-binding fragment thereof of claim 1, said antibody being a monoclonal antibody.

4. The antibody or an antigen-binding fragment thereof of claim 1, said antibody being a chimeric antibody.

5. The antibody or an antigen-binding fragment thereof of claim 1, said antibody being a humanized antibody.

6. The antibody or an antigen-binding fragment thereof of claim 1, wherein said antigen-binding fragment is selected from the list consisting of Fv, scFv, Fab, F(ab')2, Fab', scFv-Fc, diabodies, and any antigen-binding fragment whose half-life has been increased by chemical modification with polyalkylene glycol.

7. The antibody or an antigen-binding fragment thereof of claim 1, wherein said antibody is capable of inhibiting the interaction of IL-34 with at least one of its receptors.

8. The antibody or an antigen-binding fragment thereof of claim 1, wherein said antibody is capable of inhibiting the interaction of IL-34 with at least one of the receptors selected from the group consisting of Macrophage Colony Stimulating Factor Receptor (M-CSF-R) and Receptor Protein Tyrosine Phosphatase β/ζ (RPTPβ/ζ).

9. The antibody or an antigen-binding fragment thereof of claim 1, wherein the dissociation constant (KD) of said antibody is $KD \leq 10^{-11}$ M measured by BIAcore.

10. A pharmaceutical composition comprising the antibody or an antigen-binding fragment thereof of claim 1, and a pharmaceutically-acceptable carrier.

11. A medicament comprising the antibody or an antigen-binding fragment thereof of claim 1.

12. A kit comprising at least the antibody or an antigen-binding fragment thereof of claim 1.

13. The kit according to claim 12, wherein said antibody or antigen-binding fragment thereof is labelled.

14. A method for production of an antibody or an antigen-binding fragment thereof of claim 1, said method comprising the steps of:
    a) growing a host cell comprising a vector expressing:
        a.1) a nucleic acid coding for the antibody or an antigen-binding fragment thereof of claim 1;
        a.2) a nucleic acid comprising the DNA sequences of SEQ ID NO: 9, SEQ ID NO: 10, SEQ ID NO: 11, SEQ ID NO: 12, SEQ ID NO: 13 and SEQ ID NO: 14; or
        a.3) a nucleic acid comprising a DNA sequence consisting of a pair of polynucleotides, wherein one of the polynucleotides encodes the light chain and is set forth in SEQ ID NO: 15 and the other polynucleotide encodes the heavy chain and is set forth in SEQ ID NO: 16,
    in an appropriate medium, and
    b) recovering said antibody.

15. A method for treating a disease dependent on IL-34 selected from the list consisting of an inflammatory disease, auto-immune disease, cancer, and bone disease, comprising administering to a subject in need thereof: an effective amount of the antibody or an antigen-binding fragment thereof of claim 1, or a pharmaceutical composition comprising the antibody or an antigen-binding fragment thereof of claim 1 and a pharmaceutically-acceptable carrier.

16. The method according to claim 15, wherein said inflammatory disease dependent on IL-34 is selected from the list consisting of rheumatoid polyarthritis, periodontitis, periprosthetic osteolysis, Gougerot-Sjögren syndrome, arthritis, inflammatory skin pathologies, inflammatory bowel diseases and fibrosis.

17. The method according to claim 15, wherein said cancer dependent on IL-34 is selected from the list consisting of:
    tumour osteolysis,
    bone metastases,
    brain cancers,
    lung cancer, and
    bone sarcomas selected from osteosarcoma and Ewing's sarcoma.

* * * * *